(12) United States Patent
Kuwata

(10) Patent No.: US 8,603,775 B2
(45) Date of Patent: Dec. 10, 2013

(54) METHOD OF DISULFIDE CROSSLINK FORMING IN VITRO PROTEIN SYNTHESIS

(75) Inventor: Hidefumi Kuwata, Tokyo (JP)

(73) Assignee: Biocomber Co., Ltd., Tokyo (JP)

( * ) Notice: Subject to any disclaimer, the term of this patent is extended or adjusted under 35 U.S.C. 154(b) by 1633 days.

(21) Appl. No.: 11/587,899

(22) PCT Filed: Apr. 28, 2005

(86) PCT No.: PCT/JP2005/008571
§ 371 (c)(1),
(2), (4) Date: Oct. 27, 2006

(87) PCT Pub. No.: WO2005/105994
PCT Pub. Date: Nov. 10, 2005

(65) Prior Publication Data
US 2009/0162884 A1    Jun. 25, 2009

(30) Foreign Application Priority Data
Apr. 30, 2004 (JP) ................................. 2004-136520

(51) Int. Cl.
C12P 21/06 (2006.01)
(52) U.S. Cl.
USPC ........................................ 435/68.1; 435/69.1
(58) Field of Classification Search
USPC ................................................ 435/68.1, 69.1
See application file for complete search history.

(56) References Cited

U.S. PATENT DOCUMENTS

| | | | |
|---|---|---|---|
| 6,548,276 B2 | 4/2003 | Swartz et al. | |
| 2002/0123101 A1 | 9/2002 | Inoue et al. | |
| 2003/0113835 A1 | 6/2003 | Imamura et al. | |

FOREIGN PATENT DOCUMENTS

| | | |
|---|---|---|
| EP | 1 489 188 A1 | 12/2004 |
| JP | 2003-102495 A | 4/2003 |
| JP | 2003-116590 A | 4/2003 |
| WO | WO-02/053582 A2 | 7/2002 |
| WO | WO-03/072796 A1 | 9/2003 |

OTHER PUBLICATIONS

Scheele et al. "Conformational changes associated with proteolytic processing of presecretory proteins allow glutathione-catalyzed formation of native disulfide bonds", JBC, 1982, 257(20):12277-12282.*
Wilson et al. "Protein disulfide isomerase acts as a molecular chaperone during the assembly of procollagen", JBC, 1998, 273(16):9637-9643.*
Shimizu et al. "Cell-free translation reconstituted with purified components", Nature Biotechnology, 2001, 19:751-755.*
Yoshihiro Shimizu et al., Nat. Biotechnol., 2001, vol. 19, pp. 751-755.
Yugo Iwasaki et al., Journal of Bioscience and Bioengineering, vol. 89, No. 5, pp. 506-508, 2000.
FEBS Letters 514 (2002), pp. 290-294.
Lyubov A. Ryabova et al., Nature Biotechnology, vol. 15, Jan. 1997, pp. 79-84.
Ralf Jacob et al., The Journal of Biological Chemistry, vol. 270, No. 31, pp. 18678-18684 1995.
Mamadi Yilla et al., J. Cell. Bol., 1992, vol. 118, pp. 245-252.
Bulleid et al., Biochem, J., vol. 254, No. 3, p. 805-810 (Sep. 15, 1988).
Sevier et al., Nature Reviews, vol. 3, pp. 836-847 (Nov. 2002).
Tsuji et al., Biochemistry, vol. 26, No. 11, pp. 3129-3134 (Jun. 2, 1987).
Ibbetson et al., The Biochemical Journal, vol. 159, No. 2, pp. 377-384 (Nov. 1976).

* cited by examiner

*Primary Examiner* — Bin Shen
(74) *Attorney, Agent, or Firm* — Birch, Stewart, Kolasch & Birch, LLP

(57) ABSTRACT

It is an objective of the present invention to provide a method of synthesizing a protein having disulfide bonds using a reconstituted protein synthesizing system in a convenient manner with high efficiency. It has been found that a protein having the activity can be obtained and synthesized with good efficiency by using a reconstituted protein synthesizing system comprising purified components, from which enzymes and substrates influencing an oxidation-reduction state are removed and in which a state of redox equilibrium between disulfide and thiol is artificially regulated. Such system is used instead of a cell extract or a crude fraction thereof that contains various enzymes and substrates that maintain a reduced state, such as thioredoxin reductase [EC 1.6.4.5] and glutathion reductase [EC 1.6.4.2], resulting in difficulty in conditioning a redox state.

11 Claims, 14 Drawing Sheets
(2 of 14 Drawing Sheet(s) Filed in Color)

METHOD OF DISULFIDE CROSSLINK FORMING IN VITRO PROTEIN SYNTHESIS

TECHNICAL FIELD

The present invention relates to a protein synthesis method using an in vitro transcription/translation system. More specifically, the present invention relates to a method of synthesizing a protein having intermolecular/intramolecular disulfide bonds using an in vitro transcription/translation system with efficiency.

BACKGROUND ART

It has been widely attempted to produce a protein that can be used as a pharmaceutical and a reagent via gene recombination technology. Preferably, in view of the ease of handling and efficiency, microorganisms such as E. coli, Bacillus subtilis, molds, and yeasts, insects such as silkworms, mammalian animals such as bovines, and culturable plant, insect, and animal cells have recently been used in gene recombination technology. A method of producing a protein using gene recombination technology has been widely used. However, the use of such method results in, for example, a low expression level for a protein of interest, the expression of a proteins having no activity, and formation of aggregates, which have been problematic. Thus, it is necessary to carry out a trial-and-error process such as examination of culture conditions, growth conditions, or induction conditions, or testing of various types of expression systems. Even after examination of these various conditions, many proteins that are difficult to produce have been reported.

Meanwhile, a protein synthesis method that does not use any such organisms or cells, called "cell-free protein synthesis," has been known. Such cell-free protein synthesizing system is also described as an "in vitro transcription/translation system." With this system, a template gene is subjected to transcription/translation using an extract or a crude fraction thereof prepared from E. coli, rabbit reticulocytes, wheat germ cells, or the like, resulting in protein synthesis. A cell-free protein synthesizing system is characterized in that limitations associated with the use of organisms and cells can be overcome. This is because, with the use of such system, there is a high probability that a protein that disturbs functions of organisms and cells can be synthesized, various types of proteins can be synthesized using a 96-well or 384-well format, and a variety of synthesis reaction conditions can be simultaneously examined.

However, it has been known that, even with the use of such cell-free protein synthesizing system, synthesized proteins form aggregates and do not constitute the relevant original structures, which have been problematic. For that reason, it is considered that proteins having intramolecular and/or intermolecular disulfide bonds are unable to properly crosslink between disulfide bonds. There are proteins having intramolecular and/or intermolecular disulfide bonds and those not having the same. Many of proteins that are transported and secreted onto the cellular surface or into the extracellular environment have disulfide bonds. Such proteins are believed to have particularly useful application. For instance, most of protein preparations such as insulin, cytokine, and blood cell growth factors that have been commercially available have a protein having intramolecular disulfide bonds as a component.

Thus far, in order to produce such proteins having intramolecular/intermolecular disulfide bonds with good efficiency, cell-free protein synthesizing systems have been improved. For instance, the following methods have been carried out: a method of adding microsome fractions to a cell extract (Non-Patent Document 1: Biochem. J. 254:805-810 (1988), hereafter referred to as Prior art 1); and a method of dialyzing a cell extract, a method of adding oxidized glutathione and reduced glutathione, a method of gel filtration, or a method of regulating oxidation-reduction (redox) potential (Non-Patent Document 2: FEBS Lett. 514:290-4 (2002); Non-Patent Document 3: Nature Biotech. 15:79-84 (1997); Patent Document 1: JP Patent Publication (Kokai) No. 2003-116590; Patent Document 2: WO 03/072796 A1, hereafter referred to as Prior art 2).

Also, a method of disulfide bond formation using a deletion variant of an enzyme that maintains a reduced state has been known (Proc. Natl. Acad. Sci. 96: 13703-13708 (1999), hereafter referred to as Prior art 3). With this method, a protein of interest can be expressed using E. coli lacking thioredoxin reductase and glutathion reductase. However, in general, such an enzyme-deficient cell line grows very slowly or requires specific culture conditions, which have been significant obstacles in terms of industrial availability. Such method employs a system that causes gene recombination to be carried out in E. coli such that proteins are expressed. However, as described above, there have been various limitations associated with the direct use of organisms. In addition, many organisms contain many unidentified enzymes and substrates controlling oxidation-reduction in addition to thioredoxin reductase and glutathion reductase (Non-Patent Document 4: Nature Review Molecular Cell Biology 3: 836-847 (2002)). Thus, even if a foreign gene can be expressed using such a deletion variant or protein synthesis can be carried out in a cell-free protein synthesizing system using a cell extract of a deletion variant, stable disulfide bond formation has been considered to be difficult. Therefore, a method of treating a cell extract with iodacetamide so as to inactivate such enzymes and substrates has been known (U.S. Pat. No. 6,548,276 B2, hereafter referred to as Prior art 4). In accordance with this method, it is possible to inactivate not only glutathion reductase and thioredoxin reductase but also many enzymes and substrates regulating intracellular oxidation-reduction. However, since iodacetamide modifies thiol in a nonspecific manner, it also modifies factors and enzyme groups related to transcription/translation, ribosomal protein, and the like. It is considered that efficiency or accuracy of an in vitro protein synthesis reaction deteriorates as a result, which is problematic.

Meanwhile, in accordance with a method that has been widely used, proteins obtained via recombinant production using organisms and cells, chemically synthesized peptides, or proteins synthesized via a cell-free protein synthesizing system are completely denatured using a denaturant, followed by regeneration thereof (Non-Patent Document 5: Biochemistry 26:3129-3134 (1987), hereafter referred to as Prior art 5). In the case of Prior art 5, since proteins are chemically synthesized or recovered as inactive insoluble matter when using organisms, toxic proteins can be produced, for example. Upon protein regeneration, cells are not used and reagents and salts freely combine with each other so that a proper disulfide bond can be introduced into a protein having disulfide bonds. When carrying out this method, however, separate steps of protein synthesis and protein structure regeneration are required, and protein structure regeneration is a time-consuming step (taking several days to one week), which have been problematic.

Further, in accordance with a method of measuring activity of an enzyme catalyzing promotion and/or isomerization of disulfide bonds that has been widely known, ribonuclease A (RNaseA) serving as a substrate is reduced so as to be denatured, RNaseA is refolded together with an enzyme, the activity of which is measured, so as to be regenerated, and the activity of RNase obtained is determined to be an index (Non-Patent Document 6: Biochem J. 1976 159:377-384).

Patent Document 1: JP Patent Publication (Kokai) No. 2003-116590 A
Patent Document 2: WO 03/072796 A1
Patent Document 3: U.S. Pat. No. 6,548,276 B2
Non-Patent Document 1: Biochem. J. 254:805-810 (1988)
Non-Patent Document 2: FEBS Lett. 514:290-294 (2002)
Non-Patent Document 3: Nature Biotech. 15:79-84 (1997)
Non-Patent Document 4: Nature Review Molecular Cell Biology 3:836-847 (2002)
Non-Patent Document 5: Biochemistry 26:3129-3134 (1987)
Non-Patent Document 6: Biochem J. 159:377-384 (1976)

DISCLOSURE OF THE INVENTION

[Protein Synthesis]

Conventional cell-free protein synthesizing systems have had the following drawbacks upon production of proteins having intramolecular and/or intermolecular disulfide bonds. In the case of Prior art 1, it is considered that: it is necessary to prepare microsome fractions from the pancreas or the like via homogenization and centrifugation; microsome fractions are obtained by disrupting organella called endoplasmic reticula in which intracellular disulfide bond formation originally takes place so that disulfide bond formation in microsome fractions is less efficient than that in endoplasmic reticula; and patterns of disulfide bonds formed differ from original patterns, so that the protein activity might not be observed, which have been problematic. In the case of Prior art 2, it is not necessary to prepare microsome fractions, and cell extracts can be prepared via a simple method such as addition of oxidized glutathione and reduced glutathione or dialysis. However, it has been difficult to prepare a reaction solution with good reproducibility of an oxidation-reduction state such that disulfide bonds can be crosslinked with good efficiency. This is because a cell extract that is usually used as a cell-free protein synthesizing system contains various types of enzymes and substrates maintaining a reduced state, including thioredoxin reductase [EC 1.6.4.5] and glutathion reductase [EC 1.6.4.2] (Nature Review Molecular Cell Biology 3:836-847 (2002)). Thus, it is considered that functions of such enzymes and substrates cause difficulties in conditioning an oxidation-reduction state, even with dialysis or addition of glutathione. When an oxidant such as oxidized glutathione (GSSG) is added to a cell-free protein synthesizing system, a redox buffer of GSSG and reduced glutathione (GSH) has been used. Usually, the ratio therebetween is about GSSG:GSH=1:5 to 1:10. This ratio is based on oxidant concentrations and ratios obtained from a variety of studies wherein RnaseA or lysozyme is reductively denatured for refolding so as to examine the correlation between structure and activity (Biochemistry 1991 30:613-619; Biochemistry 1970 9:5015-5023)). Thus, such ratio is not necessarily suitable for a cell-free protein synthesizing system. In addition, the term "oxidation-reduction potential" indicates potential derived from differences in the chemical potentials of an oxidized form and a reduced form, which is measured using an electrode such as a platinum electrode in an equilibrium state in which reversible electron transfer is achieved. Such potential is merely obtained based on the collective observation of potentials of various inorganic/organic substances (e.g., oxygen, metal, cysteine, and heme) in a redox equilibrium state, which are involved in oxidation-reduction in a solution. Thus, it is not an index showing a state of equilibrium between thiol and disulfide and thus it does not reflect a redox state of protein. Therefore, it has been significantly difficult to regulate disulfide bond formation in proteins even if an oxidation-reduction potential could be simply adjusted to a given level as shown in Prior art 2.

In both cases of Prior arts 1 and 2, protein synthesis efficiency itself might decrease, which is problematic. This is because, when a cell extract is subjected to treatments such as addition of microsomes, dialysis, or addition of oxidized glutathione and reduced glutathione, the intracellular environment becomes different from the original intracellular environment in which protein synthesis takes place. Thus, the use of a cell-free protein synthesizing system has been significantly difficult at an industrial level.

The inventors of the present invention have already disclosed a method wherein a part or all of protein components constituting a reaction system of a cell-free in vitro DNA transcription/translation system or RNA translation system are labeled with one of a pair of substances that adhere to each other (JP Patent Publication (Kokai) No. 2003-102495 A, hereafter referred to as reconstituted protein synthesizing system). This method completely differs from conventional cell-free systems and in vitro protein synthesizing systems (hereafter to be referred to as cell-free protein synthesizing systems). Specifically, the method is characterized in that different components involved in protein synthesis are purified without using a cell extract so as to be reconstituted such that protein synthesis is achieved, resulting in synthesis or rapid purification of proteins having no intramolecular disulfide bonds (Nature Biotechnology 19:732-734 (2001)). However, it has not been reported at what concentrations different components should be reconstituted in a manner such that proteins having intramolecular/intermolecular disulfide bonds can obtain their original structures and activities and can be synthesized with good efficiency.

Thus, a more convenient method of efficiently producing proteins having intramolecular and/or intermolecular disulfide bonds has been awaited. It is an objective of the present invention to provide a method of producing proteins having disulfide bonds using a reconstituted protein synthesizing system in a convenient manner with good efficiency.

[Enzyme Activity Measurement]

In accordance with the aforementioned conventional methods, it is required that RNaseA be temporarily denatured, and the step of refolding is time-consuming, which have been problematic.

[Protein Synthesis Method]

As a result of intensive studies in order to attain the above objective, the inventors of the present invention have found that a protein having intramolecular/intermolecular disulfide bonds and its original structure and activity can be obtained and synthesized with good efficiency by using a reconstituted protein synthesizing system from which enzymes and substrates influencing an oxidation-reduction state are removed and in which a state of redox equilibrium between disulfide and thiol is artificially regulated. This system is used instead of a cell extract or a crude fraction thereof that contains various enzymes and substrates that maintain a reduced state, such as thioredoxin reductase [EC 1.6.4.5] and glutathion reductase [EC 1.6.4.2], resulting in difficulty in conditioning a redox state.

Further, the inventors of the present invention have found that it is particularly preferable that a reconstituted protein synthesizing system be composed of ribosomes, initiation factors, elongation factors, termination factors, aminoacyl-tRNA synthetases, methionyl tRNA transformylases, tRNAs, amino acids, ribonucleoside triphosphates, 10-formyl 5,6,7,8-tetrahydrofolic acid (FD), salts, and water, which have purities of 90% or more. This has led to the completion of the present invention.

In general, at an intracellular protein synthesis site, a redox state is close to a reduced state, so that proteins synthesized in cells exist in a reduced state. In a cell-free protein synthesizing system, such intracellular state is reproduced so that DTT and other reducing reagents are generally contained in the system. However, it has been reported that, when reducing reagents are not contained, the quality of a preserved extract deteriorates or translational efficiency deteriorates (Eur. J. Biochem. 270:4780-4786 (2003)).

Meanwhile, in order to form disulfide bonds with thiol, a reduced state is not desirable. Thus, it has been attempted to remove DDT as a reductant from an in vitro transcription/translation system, or to decrease the amount of DTT added to such system for formation of disulfide bonds in proteins. However, as described above, the effects obtained have been limited.

On the other hand, in accordance with the method of the present invention, since the quantity of a component influencing a state of equilibrium between disulfide and thiol in a reconstituted protein synthesizing system is identified, DTT can be added in amounts of several μM to 1 mM. In addition, it is also possible not to add any DTT.

Moreover, in general, it has been considered that, in accordance with the conventional method using a cell-free protein synthesizing system from which DTT is removed, the amount of proteins synthesized decreases and the efficiency of synthesizing proteins of interest having activities deteriorates, even under a condition in which disulfide bonds can be formed in proteins. However, surprisingly, when a reconstituted protein synthesizing system is used as described in the present invention, the amount of proteins synthesized is not changed, or increases instead so that proteins can be synthesized with improved efficiency.

That is, in accordance with the present invention, unlike the conventional methods, a method of synthesizing proteins having disulfide bonds with high efficiency is provided, wherein: a protein synthesis reagent is reconstituted with ribosomes, initiation factors, elongation factors, termination factors, aminoacyl-tRNA synthetases, methionyl tRNA transformylases, tRNAs, amino acids, ribonucleoside triphosphates, 10-formyl 5,6,7,8-tetrahydrofolic acid (FD), salts, and water, which have been specified in terms of quantity and purity and contain no impurities influencing a redox state, without using a cell extract; and a state of redox equilibrium between disulfide and thiol is artificially conditioned in the reconstituted protein synthesizing system.

In addition, preferably, the aforementioned reconstituted protein synthesis reagent is reconstituted so as to contain predetermined amounts of ribosomes, initiation factors, elongation factors, termination factors, aminoacyl-tRNA synthetases, methionyl tRNA transformylases, tRNAs, amino acids, ribonucleoside triphosphates, 10-formyl 5,6,7,8-tetrahydrofolic acid (FD), salts, and water, which are highly purified and have purities of 90% or more. As an example of a protein synthesis reagent, a Pure system (Post Genome Institute Co., Ltd.) from which DTT has been removed can be used. In accordance with the aforementioned protein synthesis method, a state of redox equilibrium between disulfide and thiol can be artificially conditioned by adding (i) a reagent for conditioning a redox state and/or (ii) an enzyme catalyzing oxidation-reduction to the above protein synthesis reagent. Such addition may be carried out before the initiation of a reaction, during the reaction, or after the reaction.

More specifically, examples of (i) a reagent for conditioning a redox state include DTT and oxidized glutathione. Further, examples of (ii) an enzyme catalyzing oxidation-reduction include protein disulfide isomerases and disulfide interchange proteins.

In addition, the method of protein synthesis of the present invention may be referred to as a method of producing proteins.

[Method of Protein Activity Measurement and a Method of Protein Synthesis Using the Same]

Further, in accordance with the present invention, a test method is provided, comprising measurement of correlations among the activity of a protein produced, the amount of an oxidoreductase reagent catalyzing oxidation-reduction to be added, and the amount of a redox reagent catalyzing oxidation-reduction to be added. A protein synthesis reagent is reconstituted with predetermined amounts of ribosomes, initiation factors, elongation factors, termination factors, aminoacyl-tRNA synthetases, methionyl tRNA transformylases, tRNAs, amino acids, ribonucleoside triphosphates, 10-formyl 5,6,7,8-tetrahydrofolic acid (FD), salts, and water, which have been specified in terms of quantity and purity. Preferably, the concentrations of an oxidoreductase reagent and redox reagent that catalyze oxidation-reduction can be varied in the protein synthesis reagent. As described above, by adding reagents capable of changing a state of redox equilibrium to a reconstituted protein synthesizing system at desired final concentrations, it becomes possible either to form or not to form disulfide bond crosslinking in proteins produced.

That is, in accordance with the present invention, it becomes possible to properly know conditions required for producing proteins exhibiting desired crosslink formation of disulfide bonds using a reconstituted protein synthesizing system. The thus obtained information can be used with regard to the aforementioned protein synthesis conditions.

An oxidoreductase reagent and a redox reagent may be added before the initiation of a reaction, during the reaction, or after the reaction.

Examples of an oxidoreductase reagent include DTT and GSSG. Examples of a redox reagent include protein disulfide isomerases and disulfide interchange proteins.

Reagents at different concentrations can be prepared in advance so as to be added to respective reaction systems before the initiation of a reaction (before addition of a template nucleic acid), during the reaction, or after the termination of the reaction.

[Method of Enzyme Activity Measurement]

Specifically, a method of activity measurement may be carried out using the aforementioned protein synthesizing system in the manner described above except that an enzyme catalyzing promotion and/or isomerization of disulfide bonds, the activity of which is measured, is added upon or after translation. Proteins used as substrates are added as template DNAs or RNAs encoding such proteins. Types of proteins used as substrates are not particularly limited. Preferably, such proteins have known structures, and more preferably, they are enzymes. Examples of such substrates include lysozyme and alkaline phosphatase. In addition, in accordance with this method, the activity of an enzyme promoting disulfide bond formation and/or catalyzing disulfide bond isomerization can be measured, while on the other hand, a substance that inhibits the activity can also be screened for. In the case of screening, screening can be carried out using a test substance with an enzyme promoting disulfide bond formation or catalyzing disulfide bond isomerization.

[Kit]

Further, the present invention includes a kit comprising the following (1) a) and b), (2) a) and c), or (3) a), b), and c):

a) a protein synthesis reaction reagent comprising components that have been specified in terms of quantity and purity and causing a reaction to synthesize a protein encoded by a template nucleic acid upon addition of the template nucleic acid;

b) at least one oxidoreductase catalyzing oxidation-reduction, which has been specified in terms of quantity and purity; and c) at least one redox reagent for conditioning a redox state, which has been specified in terms of quantity and purity.

Specifically, in accordance with the present invention, a kit comprising the following a) to c) is provided: a) protein synthesis reaction reagent comprising ribosomes, initiation factors, elongation factors, termination factors, aminoacyl-tRNA synthetases, methionyl tRNA transformylases, tRNAs, amino acids, ribonucleoside triphosphates, 10-formyl 5,6,7,8-tetrahydrofolic acid (FD), salts, and water, which have been specified in terms of quantity and purity and causing a reaction to synthesize a protein encoded by a template nucleic acid upon addition of the template nucleic acid; b) at least one oxidoreductase catalyzing oxidation-reduction, which has been specified in terms of quantity and purity; and c) at least one redox reagent for conditioning an oxidation-reduction state, which has been specified in terms of quantity and purity.

This description includes part or all of the contents as disclosed in the description of Japanese Patent Application No. 2004-136520, which is a priority document of the present application.

BRIEF DESCRIPTION OF THE DRAWINGS

The patent or application file contains at least one drawing executed in color. Copies of this patent or patent application publication with color drawing(s) will be provided by the office upon request and payment of the necessary fee.

BEST MODE FOR CARRYING OUT THE INVENTION

Figure 1:
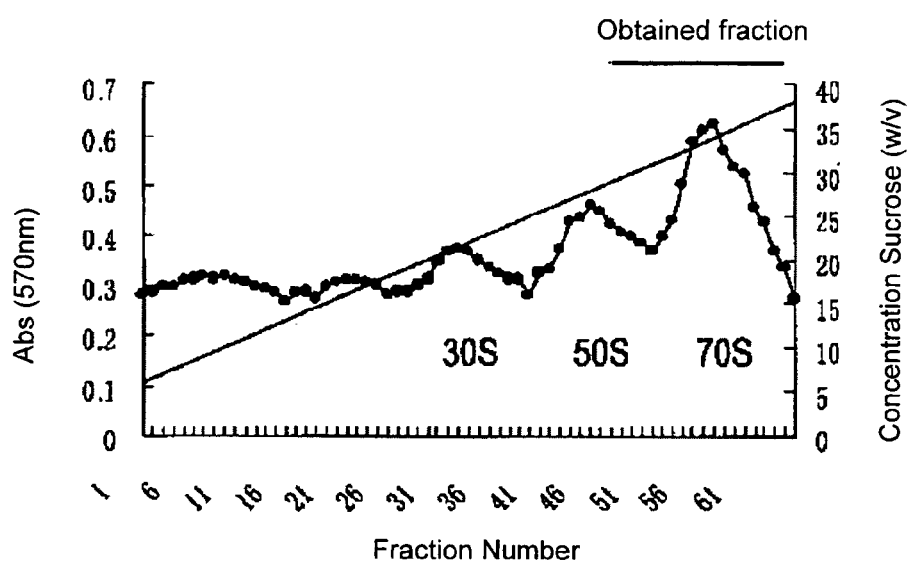
FIG. 1 shows 6% to 36% sucrose density-gradient fractions of a ribosome crude extract.

The preferred embodiments of present invention will be hereafter described in greater detail, although the technical scope of the present invention is not limited thereto. Further, all modifications and variations are within the scope of the present invention.

The in vitro DNA transcription/translation system or RNA translation system of the present invention comprises a protein synthesis reagent comprising base components for protein synthesis caused by adding a template encoding a protein of interest such as mRNA, cDNA, or the like and (i) a reagent for conditioning a redox state and/or (ii) an enzyme catalyzing oxidation-reduction so as to artificially condition a state of redox equilibrium between disulfide and thiol.

[Method of Synthesizing a Protein Having Intermolecular or Intramolecular Disulfide Bonds]

The method of the present invention include a method of synthesizing a protein having intermolecular or intramolecular disulfide bonds, comprising using (1) a reaction system comprising a) and b) below, (2) a reaction system comprising a), b), and c) below, (3) a reaction system comprising a), b), and d) below, or (4) a reaction system comprising a), b), c), and d) below:

a) at least one template nucleic acid encoding a protein of interest;

b) a protein synthesis reaction reagent comprising a plurality of components that have been specified in terms of quantity and purity and causing a reaction to synthesize a protein encoded by a template nucleic acid upon addition of the template nucleic acid;

c) at least one oxidoreductase catalyzing oxidation-reduction, which has been specified in terms of quantity and purity; and d) at least one redox reagent for conditioning a redox state, which has been specified in terms of quantity and purity.

[1-1 Protein Synthesis Reagent]

The protein synthesis reagent is characterized in that it comprises, as components, predetermined amounts of ribosomes, initiation factors, elongation factors, termination factors, aminoacyl-tRNA synthetases, methionyl tRNA transformylases, tRNAs, amino acids, ribonucleoside triphosphates, 10-formyl 5,6,7,8-tetrahydrofolic acid (FD), salts, and water, which have been specified in terms of purity. However, it does not need to contain all components described above, so that it may selectively contain the components according to need.

The components used that constitute the system must not include a cell extract or crude fractions of such a cell extract. In addition, it is desired that the concentration of a substance influencing disulfide bond formation in proteins can be calculated.

In the reconstituted protein synthesizing system of the present invention, all components that constitute the system are reconstituted. Thus, it is easy to specify such components and calculate contents thereof.

The protein synthesis reaction reagent of the present invention can be used as a reaction system for protein synthesis in which DNA transcription/translation or RNA translation is carried out. In the present invention, the term "protein" indicates two or more amino acids binding to each other via peptide bonds, including peptides, oligopeptides, and polypeptides. The term "RNA" includes chemically synthesized RNA and mRNA. The term "DNA" indicates synthesized DNA, DNA vectors, genomic DNA, PCR products, and cDNA.

The condition that the protein synthesis reaction reagent of the present invention comprises components that have been specified in terms of quantity and purity refers to each component being independently purified such that the purity thereof can be calculated and the component can be quantified. In the present invention, the plurality of components that have been specified in terms of quantity and purity are substances that have been separately purified in advance via methods for purifying substances such as salting out, chromatography, electrophoresis, solubility difference, recrystallization, and centrifugation. The purities of such substances obtained via analysis methods using chromatography, electrophoresis, mass spectrometric analysis, centrifugation, and the like are about 80% or more and more preferably 90% or more. For instance, in the case of a protein, it is purified mainly via chromatography and the purity is measured via SDS-polyacrylamide gel electrophoresis (SDS-PAGE). In the case of a ribosome, it is purified mainly via ultracentrifugation and the purity is measured by sedimentation analysis via ultracentrifugation. A ribosome is an aggregated molecule having a molecular weight of several millions, comprising a plurality of RNA molecules (3 types of RNA molecules in prokaryotes: 23S, 5S, and 16S; and 4 types of RNA molecules in eukaryotes: 28S, 5.8S, 5S, and 18S) and a plurality of ribosomal proteins (about 50 proteins in prokaryotes and about 80 proteins in eukaryotes). As an aggregated molecule, it is subjected to sedimentation analysis so as to be identified and subjected to the measurement of the purity thereof. In addition, tRNAs are molecules that usually comprise 74 to 94 nucleotides and have a plurality of nucleotide sequences. Their purities can be measured by isolating the molecules via electrophoresis for identification and measuring absorbances at 260 nm and 280 nm. In addition, low-molecular weight substances such as amino acids and salts are identified via conventional methods such as chromatography, melting point measurement, elementary analysis, and mass spectrometric analysis such that the purities thereof can be measured.

Examples of factors and enzymes for transcription/translation as protein synthesis reagents that can be used include not only those derived from prokaryotic cells such as E. coli and but also those derived from eukaryotic cells:

(1) in the case of translation based on RNA, ribosomes, initiation factors, elongation factors, termination factors, aminoacyl-tRNA synthetases, tRNAs, adenosine triphosphate (ATP), guano sine triphosphate (GTP), amino acids, 10-formyl 5,6,7,8-tetrahydrofolic acid (FD), salts, and water are included, and methionyl tRNA transformylases are further included in the case of a reaction system derived from prokaryotic cells such as E. coli; and (2) in the case of transcription/translation based on DNA, uridine triphosphate (UTP), cytidine triphosphate (CTP), and RNA polymerases such as T7RNA polymerase are included in addition to (1).

Various types of factors and enzymes constituting the reaction system of the present invention are originally contained in any organisms such as E. coli, molds, yeasts, and cultured cells. Thus, they can be separately purified at a high level so as to be used as components. However, recombinant products are preferably used because this allows each type of protein to be obtained in large volume, and unknown unnecessary or inhibitory components are less likely to be brought into the reaction system.

Specifically, genes encoding initiation factors, elongation factors, termination factors, aminoacyl-tRNA synthetases, methionyl tRNA transformylases, or RNA polymerases are ligated to adequate vectors, followed by transformation using E. coli, Bacillus subtilis, mold, yeast, or the like for expression induction. Then, the proteins are purified such that components constituting the reaction system of the present invention can be obtained. When various types of factors and enzymes are produced using transformants, proteins may be expressed as being intact or may be expressed as fusion proteins. Examples of a fusion protein include a Histidine-Tag (hereafter referred to as His-Tag), a strept-Tag, a GST-Tag, and a FLAG-Tag (Appl Microbiol Biotechnol. 60 (5): 523-533 (2003)).

Various forms of methods for purifying His-Tagged protein components using a His-Tag and a nickel column have been known can be selectively used according to need. As an example, an outline of such a method is described as follows:

1. obtaining a fusion protein by allowing a His-Tag (comprising 6 His) to bind at the N-terminal of a protein of interest via a genetic engineering technique;

2. sonicating cells in which His-Tagged proteins have been expressed in ice and allowing the cells be suspended in a loading buffer (300 mM NaCl, 50 mM $NaH_2PO_4$, pH 8.0);

3. allowing the cell lysate to be subjected to centrifugation (30,000 g, 4° C., 30 minutes);

4. adding 50% $Ni^{2+}$-NTA slurry (Qiagen) equilibrated with an ice-cooled loading buffer to the supernatant obtained above, followed by stirring at 4° C. for 1 hour;

5. loading resin into a column, followed by washing using a loading buffer in a volume 20 times that of the column at 4° C.;

6. washing the column using a loading buffer (containing 10 mM imidazole, pH 8.0) in a volume 20 times that of the column at 4° C.; and 7. setting the imidazole concentration gradient to 10 to 250 mM using a loading buffer in a volume 20 times that of the column, allowing the protein of interest to be eluted from the column, collecting fractions (1 ml each), and confirming the protein of interest via SDS-PAGE.

More preferably, after purification of the protein as described above, the following enzymes that are not directly involved in protein synthesis are added to the reaction system of the present invention as various types of factors and enzymes constituting the reaction system: enzymes related to energy regeneration such as creatine kinases, myokinases, and nucleoside diphosphate kinases; and enzymes used for degradation of inorganic pyrophosphoric acids generated via a transcription/translation reaction, such as inorganic pyrophosphatases.

Herein, it is essential for salts to contain cations and anions that are necessary for transcription/translation. Examples thereof that are generally used include potassium glutamate, ammonium chloride, magnesium acetate, and calcium chloride. Needless to say, in addition to the salts described above, appropriate salts can be selectively used. Examples of water include types that do not contain ions, microorganisms, enzymes, and the like, such as water produced using a Milli-Q system (Millipore) and commercially available pure water.

Ribosomes are sites for peptide synthesis. When a ribosome binds to mRNA, aminoacyl-tRNA is located at an A site and formyl methionyl tRNA or peptidyl tRNA is located at a P site in the ribosome, such that a reaction of forming peptide bonds takes place (Science 289:920-930 (2000)). In the present invention, ribosomes having such functions can be used regardless of their origins. Examples thereof that can be used include *E. coli*-derived ribosomes and eukaryotic cell-derived ribosomes. Preferably, ribosomes that can be used in the present invention are those derived from *E. coli* such as *E. coli* A19 cells and *E. coli* MRE600 cells.

As initiation factors of the in vitro protein synthesizing system of the present invention, those derived from *E. coli* such as IF1, IF2, and IF3 have been known, which are essential for formation of a translation initiation complex or act as factors significantly promoting such formation (Biochemistry 29:5881-5889 (1990)). The initiation factor IF3 promotes dissociation of a 70S ribosome into a 30S subunit and a 50S subunit, which is a necessary step for translation initiation. In addition, it inhibits insertion of tRNA excluding formyl methionyl tRNA at the P site upon translation initiation complex formation. The initiation factor IF2 binds to formyl methionyl tRNA and transfers formyl methionyl tRNA to the P site of a 30S ribosome subunit, resulting in formation of a translation initiation complex. The initiation factor IF1 promotes functions of initiation factors IF2 and IF3. Preferred examples of initiation factors that can be used in the present invention include those derived from *E. coli* such as *E. coli* K12 cells. In addition, those derived from eukaryotic cells can also be used.

There are two types of EF-Tu elongation factors: GTP and GDP. GTP binds to aminoacyl-tRNA so as to transport the tRNA to the A site of a ribosome. When EF-Tu is leaving the ribosome, GTP is hydrolyzed so as to be converted into GDP (EMBO J. 17: 7490-7497 (1998)). Meanwhile, an EF-Ts elongation factor binds to EF-Tu (GDP) so as to promote conversion of GDP into GTP (Archives of Biochemistry and Biophysics 348: 157-162 (1997)). In addition, an EF-G elongation factor promotes a translocation reaction after a reaction of peptide bond formation during the process of peptide chain elongation (Nature Structure Biology 6:643-647 (1999); FEMS Microbiology Reviews 23:317-333 (1999)). Preferred examples of elongation factors used in the present invention are those derived from *E. coli*, such as those obtained from *E. coli* K12 cells. In addition, those derived from eukaryotic cells can also be used.

Termination factors are essential for ribosome recycling during the process of termination of protein synthesis, dissociation of peptide chains subjected to translation, and initiation of subsequent mRNA translation. When protein synthesis is carried out in a reaction system without termination factors, the reaction terminates before a termination codon so that a stable complex of a ribosome, a peptide, and mRNA is easily formed (a polysome display method, a ribosome display method, and an in vitro virus method). In addition, introduction of an unnatural amino acid into a peptide chain is carried out by omitting RF1 and/or RF2 from the reaction system. In other words, introduction of unnatural amino acid into a UAG codon and a UGA codon is carried out with high efficiency when RF1 and RF2 are omitted, respectively.

When a termination codon (UAA, UAG, or UGA) is located at the A site of a ribosome, termination factors RF1 and RF2 move to the A site so as to promote dissociation of a peptide chain from peptidyl tRNA (located at the P site). RF1 recognizes termination codons UAA and UAG, and RF2 recognizes termination codons UAA and UGA. A termination factor RF3 promotes dissociation of RF1 and RF2 from a ribosome after a reaction of peptide chain dissociation caused by RF1 and RF2. A ribosome recycling factor (RRF) promotes detachment of tRNA remaining at the P site after protein synthesis termination and ribosome recycling for subsequent protein synthesis. In the present invention, RRF is regarded as a termination factor. In addition, functions of RF1, RF2, RF3, and RRF termination factors are explained in EMBO J. 16: 4126-4133 (1997) and EMBO J. 16: 4134-4141 (1997). Preferred examples of termination factors that can be used in the present invention are those derived from *E. coli* such as those obtained from *E. coli* K12 cells. In addition, those derived from eukaryotic cells can also be used.

An aminoacyl-tRNA synthetase is an enzyme synthesizing aminoacyl-tRNA by causing covalent binding of an amino acid and tRNA in the presence of ATP (RNA 3:954-960 (1997); Protein, Nucleic Acid and Enzyme, 39: 1215-1225 (1994)). Preferred examples of an aminoacyl-tRNA synthetase that can be used in the present invention are those derived from *E. coli*, such as those obtained from *E. coli* K12 cells. In addition, those derived from eukaryotic cells can also be used. Further, an artificial aminoacyl-tRNA synthetase recognizing an unnatural amino acid can also be used (JP Patent No. 2668701).

A methionyl tRNA transformylase (MTF) is an enzyme synthesizing N-formyl methionyl (fMet) tRNA in which a formyl group has bound to an amino group of methionyl tRNA as a result of protein synthesis in prokaryotes. That is, methionyl tRNA transformylase causes a formyl group of N10-formyl tetrahydrofolic acid to be transferred to the N-terminal of methionyl tRNA corresponding to an initiation codon such that fMet-tRNA is formed (Proc. Natl. Acad. Sci. USA, 96: 875-880 (1999)). The thus added formyl group is recognized by an initiation factor IF2 so that it can function as an initiation signal of protein synthesis. MTF does not exist in a synthesis system of eukaryotic cytoplasm; however, it exists in synthesis systems of eukaryotic mitochondria and chloroplast. Preferred examples of MTF that can be used in the present invention are those derived from *E. coli*, such as those obtained from *E. coli* K12 cells.

RNA polymerase is an enzyme transcribing a DNA sequence to RNA, and it has been known to exist in various types of organisms. An example thereof is T7 RNA polymerase that is derived from T7 phage. This polymerase is an enzyme that binds to a specific DNA sequence called a T7 promoter so as to transcribe the downstream DNA sequence to RNA. The inventors of the present invention added a His-Tag to the N-terminal of T7 RNA polymerase, caused massive expression of the polymerase as a fusion protein in an *E. coli* BL21 cell line, and carried out purification via affinity chromatography using a nickel column. In the present invention, as well as T7 RNA polymerase, various types of RNA polymerases can be used. For instance, T3 RNA polymerase and SP6 RNA polymerase have been commercially available, and they can be used in the present invention.

Examples of amino acids include natural or unnatural amino acids and tRNAs charged with natural or unnatural amino acids. When using such a tRNA charged with an unnatural amino acid, an unnatural amino acid can be introduced into a protein.

Examples of tRNA that can be used include tRNA purified from cells of *E. coli*, yeast, and the like. In addition, artificial tRNA in which an anticodon or another base is optionally modified (J. Am. Chem. Soc. 121:34-40 (1996), Nature Biotech. 20: 177-182 (2002)) can be used. For instance, when tRNA having CUA as an anticodon is charged with an unnatural amino acid, a UAG codon that is a termination codon in its original form can be translated to an unnatural amino acid. Using this method, an unnatural amino acid can be introduced into a protein in a site-specific manner.

Further, as a buffer, a potassium phosphate buffer (pH 7.3) is generally used.

[1-2 Substances Influencing Disulfide Bond Formation]

Examples of substances influencing disulfide bond formation include an oxidoreductase that is an enzyme catalyzing oxidation-reduction of a disulfide bond and/or a redox reagent that is a reagent for conditioning a redox state of a disulfide bond. More specifically, examples of an enzyme and/or reagent influencing disulfide bond formation include: (i) enzymes catalyzing oxidation-reduction such as proteins, including glutathion reductases, thioredoxin reductases, protein disulfide isomerases, disulfide interchange proteins, and thioredoxin-like proteins; and/or (ii) reagents for conditioning a redox state such as low-molecular-weight compounds, including reduced glutathione, oxidatized glutathione, DTT, 2-mercaptoethanol, and thioredoxin. The term "redox reagent" of the present invention indicates a reagent that can reduce disulfide to thiol or can oxidate thiol so as to form disulfide.

Preferably, an enzyme and/or a substrate thereof promoting/regulating disulfide bond crosslinking in proteins is used as (i) an oxidoreductase (enzyme catalyzing oxidation-reduction) and/or (ii) a redox reagent (reagent for conditioning a redox state), which are substances influencing disulfide bond formation. In addition, (i) an enzyme catalyzing oxidation-reduction and/or (ii) a reagent for conditioning a redox state are not necessarily added during a translation reaction. They may be added after the termination of translation. When they are added after the termination of translation, preferably, they are allowed to stand for several tens of minutes to about an hour at 37° C. after addition.

When DTT is used as a reagent for conditioning a redox state, the concentration thereof is 0 to 1 mM, preferably 0.001 to 0.5 mM, and more preferably 0.060 to 0.5 mM.

When oxidized glutathione is used as a reagent for conditioning a redox state, the concentration thereof is 0 to 8 mM, preferably 0.1 to 4 mM, and more preferably 1 to 4 mM.

In accordance with the method for protein synthesis described above, disulfide interchange proteins are preferably DsbA and/or DsbC.

Protein disulfide isomerase (EC 5.3.4.1.) is an enzyme having a size of about 55 kDA, existing in endosporium of the endoplasmic reticulum of a eukaryote, and catalyzing formation, isomerization, and/or reduction reaction of a disulfide bond. It is considered to have chaperone-like activity. As mentioned above, this protein can be used as a component after being purified from organisms. Also, it may be obtained through recombination production for use. For instance, protein disulfide isomerase (PIR database accession no. ISBOSS) (SEQ ID NO: 5) purified from the liver of a bovine or purified proteins obtained through recombinant expression of a protein disulfide isomerase gene of yeast using $E.$ $coli$ can be used.

In addition, the following proteins have been known as protein disulfide isomerases and they can be used as protein disulfide isomerases of the present invention:

human protein disulfide-isomerase (PIR database accession no. ISHUSS) (SEQ ID NO: 6);

human protein disulfide-isomerase-related protein (GenBank accession no. 4758304) (SEQ ID NO: 7); and yeast protein disulfide isomerase homolog (PIR database accession no. A44483) (SEQ ID NO: 8).

As disulfide interchange proteins, four types of proteins called disulfide interchange proteins A, B, C, and D (DsbA, B, C, and D) have been known to exist in $E.$ $coli$ and the like. DsbA is an enzyme having a 21-kDa thioredoxin-like fold structure, and it is considered to catalyze disulfide bond formation. DsbB is a protein 20 kDa in size, which has four transmembrane regions and two periplasm domains. DsbB is considered to maintain DsbA in a state of being oxidized. DsbC is a periplasm protein that forms a homodimer and has a thioredoxin-like fold. DsbC is considered to be an enzyme that is mainly responsible for disulfide bond isomerization and to function as chaperone. DsbD is a protein having a molecular weight of 59 kDa, which comprises two periplasm domains and eight transmembrane regions. DsbD is considered to have a function of maintaining cysteine as an active center of DsbC in a state of being reduced.

The following proteins have been known as disulfide interchange proteins, and they can be used as disulfide interchange proteins of the present invention:

$E.$ $coli$ DsbA (SWISS-PROT protein database accession no. P24991) (SEQ ID NO: 9);

$E.$ $coli$ DsbC (SWISS-PROT protein database accession no. P21892) (SEQ ID NO: 10);

*Salmonella typhimurium* protein disulfide-isomerase dsbA homolog (PIR database accession no. S32895) (SEQ ID NO: 11);

*Neisseria meningitidis* thiol-disulfide interchange protein dsbA homolog NMB0278 (PIR database accession no. C81217) (SEQ ID NO: 12);

*Caenorhabditis elegans* protein disulphide isomerase isoform I (GeneBank accession no. AAB94647) (SEQ ID NO: 13); and

*Datisca glomerata* protein disulfide isomerase homolog (GeneBank accession no. AAD28260) (SEQ ID NO: 14).

As mentioned before, these disulfide interchange proteins can be purified from organisms so as to be used as components, and also, they may be obtained through recombination production for use.

When using protein disulfide isomerase (PDI) as oxidoreductase, the concentration thereof is preferably 0 to 10 µM, more preferably 0.001 to 5 µM, and further preferably 0.001 to 2 µM. When using disulfide interchange protein as oxidoreductase, the concentration thereof is preferably 0 to 10 µM, more preferably 0.01 to 10 µM, and further preferably 0.1 to 10 µM.

In addition, preferably, disulfide interchange proteins contain minimum amounts of glutathion reductases and thioredoxin reductases. Preferably, the contents of thioredoxin reductase and/or glutathion reductase in a component constituting a protein synthesizing system are 100 ng/ml or less.

In addition, a method of measuring the purity of each component described above is exemplified below.

The purity can be calculated in the following manner: the aforementioned components comprising proteins such as initiation factors, elongation factors, termination factors, methionyl tRNA transformylases, DsbA, and DsbC are purified by a method of purifying His-Tagged proteins using a His-Tag and a nickel column; proteins of interest are confirmed by SDS-PAGE; and the electrophoresis pattern of each lane is using a densitometer.

The purity of purified ribosomes can be measured via sucrose density-gradient analysis.

Reagents that have been commercially available in general such as tRNAs, amino acids, ribonucleotide triphosphates, FD, other types of buffers, DTT, and oxidized glutathione can be used at the purity level of commercially available forms of such reagents. In addition, all such commercially available reagents have a purity of 80% or more.

[Test Method and Synthesis Method Utilizing the Same]

As a test method of the present invention, the reaction system of the [method of synthesizing a protein having intermolecular or intramolecular disulfide bonds] described above can be used.

The test method of the present invention comprises measuring correlations among the concentration of an oxidoreductase, the concentration of a redox reagent, and the activity of a synthesized protein comprising at least one peptide chain, in which crosslink formation can be carried out using a single disulfide bond, and the activity of which is controlled based on the pattern of such crosslink formation. The method is carried out using a reaction system comprising the following a) to d), and specifically (1) a), b), and c), (2) a), b), and d), and (3) a), b), and c), and d):

a) at least one template nucleic acid;
b) a protein synthesis reaction reagent comprising a plurality of components that have been specified in terms of quantity and purity and causing a reaction to synthesize a protein encoded by a template nucleic acid upon addition of the template nucleic acid;
c) at least one oxidoreductase catalyzing oxidation-reduction, which has been specified in terms of quantity and purity; and
d) at least one redox reagent for conditioning a redox state, which has been specified in terms of quantity and purity.

The activity of a protein synthesized via the above reaction system is measured such that correlation among the protein, c) the oxidoreductase added, and d) the redox reagent added is determined. Herein, the protein activity to be measured is not limited to enzyme activity. For instance, binding activity between a receptor and a protein, cellular proliferation activity, specific activity between binding activity and cellular proliferation activity, and the like are included.

More specifically, c) oxidoreductases and d) redox reagents at various concentrations are prepared, upon which c) and d) may each comprise a single substance or may be a mixture of a plurality of substances. Examples of such oxidoreductases include protein disulfide isomerases, disulfide interchange proteins, and homologous enzymes. Examples of such redox reagents include DTT, GSSG, GSH, and thioredoxin. Subsequently, a protein synthesis reaction is initiated. Subsequently, a protein synthesis reaction is carried out. Herein, c) and d) may be added at the beginning of the protein synthesis reaction, may be added during the synthesis reaction, or may be added after the termination of the synthesis reaction. When c) and d) are added after the termination of the synthesis reaction, the resultant is preferably allowed to stand for several tens of minutes to an hour at about 37° C. after the addition. In each case of protein synthesis described above, the activity of a protein synthesized in a reaction solution is determined. Herein, a protein to be synthesized is not particularly limited, as long as it is a protein in which crosslink formation of at least one intramolecular and/or intermolecular disulfide bond can be achieved. For instance, a plurality of proteins are allowed to be synthesized in a single reaction solution so as to form a heterooligomer or the like, such that the activities thereof can be determined.

As described above, correlation of protein activity, c) an oxidoreductase, and/or d) a redox reagent can be revealed.

With the use of the thus obtained correlation, a protein of interest can be created with efficiency in a reaction system produced by: determining concentrations of c) an oxidoreductase and/or d) a redox reagent that are necessary to obtain a predetermined activity level (desired activity level); adding c) an oxidoreductase and/or d) a redox reagent to b) a protein synthesis reaction reagent so as to achieve a concentration at which the desired activity can be obtained; and adding a) a template nucleic acid encoding the protein of interest.

The present invention is hereafter described in greater detail with reference to the following examples, although the technical scope of the present invention is not limited thereto.

Example 1

Ribosome Preparation

Cells of an *E. coli* A19 cell line (300 g) during the middle logarithmic phase were disrupted using alumina particles. The thus disrupted cells were suspended in a buffer A (10 mM HEPES-potassium hydroxide (pH 7.6, HEPES-KOH), 10 m Magnesium chloride ($MgCl_2$), 50 mM potassium chloride (KCl), and 1 mM DTT). Then, alumina particles and disrupted cells were removed therefrom via centrifugation (30,000 g, 4° C., 1 hour). Then, deoxyribonuclease (DNase) was added to the thus obtained supernatant fraction to a final concentration of 1 μg/ml, followed by centrifugation (100,000 g, 4° C., 4 hours). The resulting pellet was suspended in a buffer A such that a crude ribosome extract was prepared. The crude ribosome extract was subjected to 6% to 36% (w/v) sucrose density-gradient centrifugation. A fraction shown in FIG. 1 resulted from fractionation. The obtained ribosome fraction was subjected to centrifugation at 100,000 g. The resulting pellet was suspended in a ribosome buffer (20 mM HEPES-KOH (pH 7.6), 6 mM MgOAc, 30 mM $NH_4Cl$, 7 mM β-mercaptoethanol (mercaptoethanol)) such that purified ribosomes were prepared. Some of purified ribosomes were subjected to 6% to 36% (w/v) sucrose density-gradient analysis such that a single peak was formed. The purity of the ribosomes was 90% or more.

Example 2

Construction of Plasmids Hyperexpressing Aminoacyl-tRNA Synthetase (ARS) and Production of Transformants Using a genome extracted from an *E. coli* A19 cell line as a template, a gene sequence encoding alanyl-tRNA synthetase was amplified by PCR such that a DNA fragment having a sequence recognized by SphI at the 5' end and HindIII at the 3' end was obtained. The obtained DNA fragment was inserted into a plasmid pQE30 (QIAGEN) that had previously been cleaved with SphI and HindIII. Thus, a vector used to cause high expression of alanyl-tRNA synthetase having a His-Tag fused at the N-terminal thereof was obtained. The thus obtained vector was used for transformation of *E. coli* BL21/pREP4. Another vector hyperexpressing ARS was constructed in a similar manner. Table 1 lists vectors, restriction enzymes, and sites of His-Tag. In addition, a series of pQE plasmids and a series of pET plasmids listed in table 1 were used for transformation of *E. coli* BL21/pREP4 and *E. coli* BL21/DE3, respectively.

TABLE 1

| Enzymes or factors | Vector | N-terminal R. E. | C-terminal R. E. | Site of His-Tag |
|---|---|---|---|---|
| AlaRS | pQE30 | SphI | HindIII | N |
| ArgRS | pET16b | NdeI | BamHI | N |
| AsnRS | pQE30 | BamHI | HindIII | N |

TABLE 1-continued

| Enzymes or factors | Vector | N-terminal R. E. | C-terminal R. E. | Site of His-Tag |
|---|---|---|---|---|
| AspRS | pET21a | NdeI | XhoI | C |
| CysRS | pET21a | NdeI | XhoI | C |
| GlnRS | pET21a | NdeI | XhoI | C |
| GluRS | pET21a | NdeI | XhoI | C |
| GlyRS | pET21a | NdeI | XhoI | C |
| HisRS | pET21a | NdeI | XhoI | C |
| IleRS | pET21a | NdeI | HindIII | N |
| LeuRs | pET21a | XbaI | XhoI | C |
| LysRS | pET21a | NdeI | XhoI | C |
| MetRS | pET21a | XbaI | XhoI | C |
| PheRS | pQE30 | SphI | HindIII | N |
| ProRS | pET21a | NdeI | XhoI | C |
| SerRS | pET21a | XbaI | XhoI | C |
| ThrRS | pQE30 | BamHI | HindIII | N |
| TrpRS | pET21a | NdeI | XhoI | C |
| TyrRS | pET21a | NdeI | XhoI | C |
| ValRS | pET21a | XbaI | NotI | C |
| MTF | pET21a | NdeI | XhoI | C |
| IF1 | pQE30 | BamHI | HindIII | N |
| IF2 | pQE30 | BamHI | HindIII | N |
| IF3 | pQE30 | BamHI | HindIII | N |
| EF-G | pQE60 | MunI | BglII | C |
| EF-Tu | pQE60 | EcoRI | BglII | C |
| EF-Ts | pQE60 | NcoI | BamHI | C |
| RF1 | pQE60 | BamHI | HindIII | C |

Note:
"R. E." stands for restriction enzyme.

Example 3

Construction of Other Plasmids Hyperexpressing Protein Factors and Enzymes

The following plasmids hyperexpressing protein factors and enzymes were constructed in a manner similar to that described in Example 2: MTF, T7 RNA polymerase, IF1, IF2, IF3, EF-G, EF-Tu, EF-Ts, and RF1. In addition, plasmids for protein factors and enzymes that are not listed in table 1 were also constructed in a similar manner. In addition, a series of pQE vectors or a series of pET vectors were used for transformation of E. coli BL21/pREP 4 or E. coli BL21/DE3.

Example 4

Hyperexpression and Purification of Protein Factors and Enzymes

Figure 2:
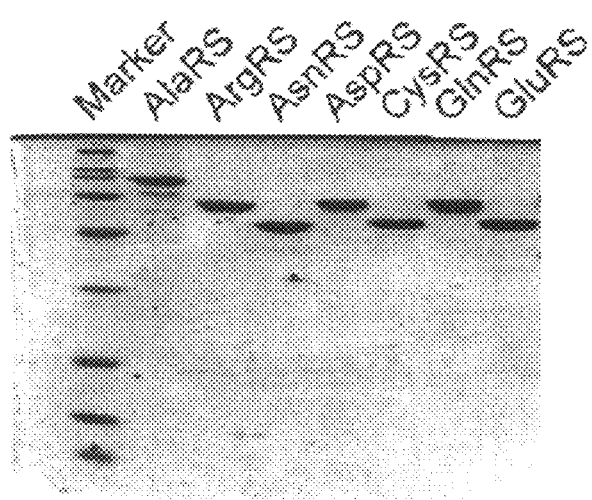
FIG. 2 shows images of His-Tagged alanyl-tRNA synthetase (AlaRS), arginine tRNA synthetase (ArgRS), asparagine tRNA synthetase (AsnRS), aspartic acid tRNA synthetase (AspRS), cysteine tRNA synthetase (CysRS), glutamine tRNA synthetase (GlnRS), and glutamic acid tRNA synthetase (GluRS) subjected to 12% SDS-PAGE/Coomassie brilliant blue staining.

In order to cause hyperexpression of His-Tagged alanyl-tRNA synthetase, E. coli BL21/pREP4 cells that were transformants obtained in Example 2 were cultured in an LB medium (6 liter) until the absorbance at 660 nm became 0.7. To the culture solution, isopropyl-1-thio-β-D-galactopyronoside (IPTG) was added to a final concentration of 0.1 mM, followed by additional culture at 37° C. for 4 hours. The culture solution was subjected to centrifugation and the obtained cells were suspended in a suspension buffer (50 mM HEPES-KOH (pH 7.6), 1 M NH$_4$Cl, 10 mM MgCl$_2$, 0.3 mg/ml albumen lysozyme, 0.1% TritonX-100, 0.2 mM phenylmethanesulfonyl fluoride (PMSF), and 6 mMβ-mercaptoethanol). The suspension was sonicated such that the cells were disrupted. The sonicated suspension was subjected to centrifugation (100,000 g, 4° C., for 1 hour). Then, disrupted cells were removed therefrom. The obtained supernatant fraction was placed in a 10-ml Hi-Trap chelating column (Pharmacia) that had been precharged with Ni$^{2+}$, followed by washing with 100 ml of an HT buffer containing 10 mM imidazole (50 mM HEPES-KOH (pH 7.6), 1M NH$_4$Cl, and 10 mM MgCl$_2$). His-Tagged alanyl-tRNA synthetase was eluted from the column with a linear gradient of 10 to 400 mM imidazole concentration in the HT buffer. Fractions containing purified proteins were dialyzed using a stock buffer (50 mM HEPES-KOH (pH 7.6), 100 mM KCl, 10 mM MgCl$_2$, and 30% glycerol). The concentration of purified His-Tagged alanyl-tRNA synthetase was calculated based on a calibration curve prepared using a Protein Assay Kit (Bio-Rad) with reference to bovine serum albumin (BSA). The purified His-Tagged alanyl-tRNA synthetase was aliquoted at 1 ml and rapidly frozen using liquid nitrogen, followed by storage at −80° C. His-Tagged alanyl-tRNA synthetase (AlaRS), arginine tRNA synthetase (ArgRS), asparagine tRNA synthetase (AsnRS), aspartic acid tRNA synthetase (AspRS), cysteine tRNA synthetase (CysRS), glutamine tRNA synthetase (GlnRS), and glutamic acid tRNA synthetase (GluRS) were purified in a similar manner. FIG. 2 shows separation of His-Tagged factors via 12% SDS-PAGE (subjected to Coomassie brilliant blue staining). The purity of each factor calculated by a densitometer was 90% or more. In addition, other factors and enzymes of table 1, which are not shown in FIG. 2, were also subjected to separation by SDS-PAGE. The purity of each factor or enzyme calculated by a densitometer in a similar manner was 90% or more.

Example 5

Translation Experimentation

General Methods

The composition of a protein synthesis reaction reagent (50 μl) was as follows: 2 mM of ATP, 2 mM of GTP, 1 mM of CTP, 1 mM of UTP, 10 mM of creatine phosphate (creatine phosphate), 2.8 A 260 unit tRNA mix, 0.5 μg of FD, 0.1 mM of each amino acid, 9 mM of magnesium acetate, 5 mM of potassium phosphate (pH 7.3), 95 mM of potassium glutamate, 5 mM of ammonium chloride, 0.5 mM of calcium chloride, 1 mM of spermidine, 8 mM of putrescine, 12 pmol of ribosome, 1 μg of IF1, 2 μg of IF2, 0.75 μg of IF3, 1 μg of EF-G, 2 μg of EF-Tu, 1 μg of EF-Ts, 0.5 μg of RF1, 0.5 μg of RF3, 0.5 μg of RRF, 30-300 units each of ARS and MTF, 0.2 μg of creatine kinase (CK), 0.15 μg of myokinase (MK), 0.054 μg of nucleoside diphosphate kinase (NDK), 1.78 units of PPiase, and 0.5 μg of T7 RNA polymerase. To this protein synthesis reaction reagent, 1 pmol of template DNA was added, followed by reaction at 37° C. for 1 hour.

When it was necessary to remove ribosomes after reaction, ribosomes were removed by allowing them to pass through an ultrafilter membrane through which substances having sizes of 100 kDa or less can pass.

In addition, ribosomes and items listed in table 1 among the items of the above composition were prepared in the manner described in Examples 1 and 4, and the purities thereof were measured. The other components used were commercially available purified reagents.

Also, when the composition described above was applied for Examples 6 to 12 described below, items listed in table 1, ribosomes, DsbA, and DsbC were prepared in the manner described in Examples 1, 4, and 13, and the purities thereof were measured. The other components used were commercially available purified reagents.

Example 6

Synthesis of Human Lysozyme

It has been reported that lysozyme is a protein that originally has four intramolecular disulfide bonds and that two or more of such disulfide bonds must be crosslinked with each other such that the activity thereof is exhibited (J Biol Chem 251:3147-3153 (1976)). Thus, lysozyme has long been widely used as a model protein with which correlation between the structure and the activity of a protein is examined. Herein, in accordance with the method of the present invention and a conventional method, human lysozyme was synthesized such that the amounts and specific activities of proteins synthesized could be examined.

From a human lysozyme cDNA clone (human gene collection, Stratagene), the following two primers were used such that a gene corresponding to matured human lysozyme having a size of 0.42 kbp was amplified by PCR: the forward primer sequence: AAGGAGATATACCAATGAAG-GTCTTTGAAAGGTGTG (SEQ ID NO: 1); and the reverse primer sequence: GGATTAGTTATTCATTACACTCCA-CAACCTTGAACAT (SEQ ID NO: 2).

Then, with the use of a forward primer having a sequence of GAAATTAATACGACTCACTATAGG-GAGACCACAACGGTTTCCCTCTAGAAATAATTT TGTTTAACTTTAAGAAGGAGATATACCA (SEQ ID NO: 3) and the above reverse primer, template DNA about 0.51 kbp in length containing a T7 promoter region was amplified by PCR. The sequence of the template DNA is set forth in SEQ ID NO: 4 in the Sequence Listing.

To each protein synthesis reaction reagent (used in the method of the present invention) described in Example 5 and 50 μl of a reaction liquid obtained by adding 1 mM of DTT to the reaction reagent (used in the conventional method), 1 pmol of prepared template DNA was added such that a protein synthesis reaction was carried out.

Figure 3:
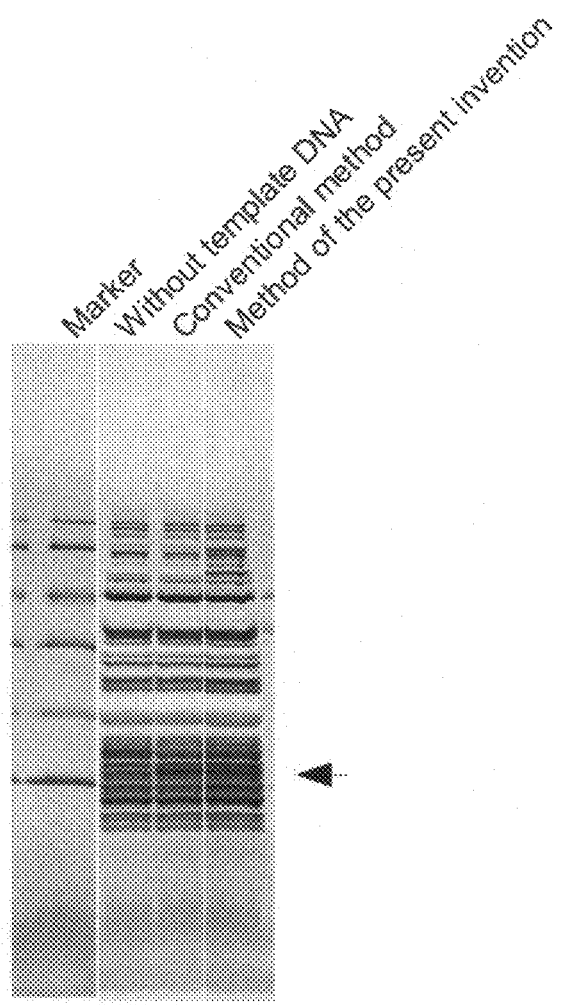
FIG. 3 shows electrophoresis images of synthesized human lysozyme (an arrow indicates synthesized human lysozyme).
Figure 4:
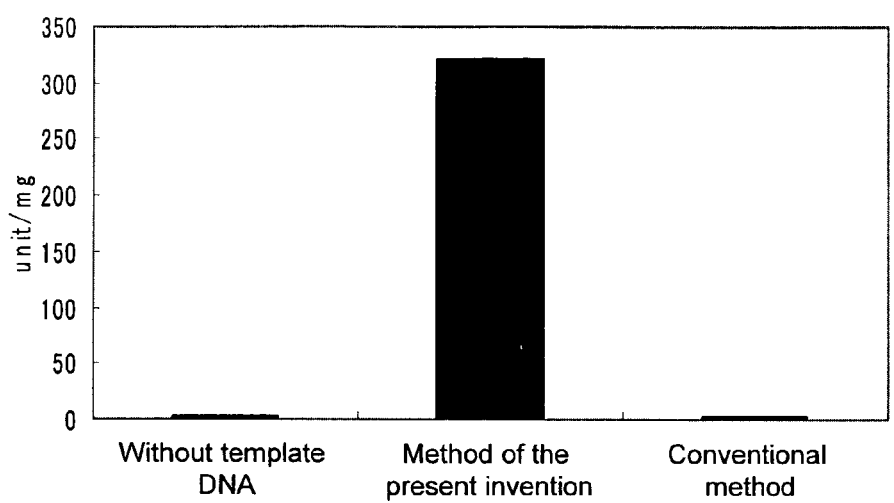
FIG. 4 shows specific activities of synthesized human lysozymes.

Synthesized proteins were separated by SDS-PAGE so as to be subjected to staining with SYPRO Orange (Amersham pharmacia). A band of human lysozyme having a molecular weight of 17000 was compared with the band of BSA having a known concentration such that the concentration of synthesized human lysozyme was obtained. The activity of human lysozyme was measured using frozen dry powders of a *Micrococcus luteus* ATCC 4698 cell line (SIGMA) under the condition that the amount that can cause a decrease in absorbance at 450 nm by 0.001 per minute was determined to be 1 unit (Imoto T., Johnson L. N., North A. T. C., Phillips D. C., Rupley J. A., The Enzymes, 3rd ed., 7, 665-868 (1972)). FIGS. 3 and 4 show an electrophoresis image and specific activities of synthesized proteins, respectively. As is apparent from FIGS. 3 and 4, in the case of the conventional method, synthesized proteins were confirmed via electrophoresis; however, no activity was confirmed. On the other hand, in the case of the method of the present invention, specific activity at about 300 units/mg was confirmed. Thus, it was found that, in accordance with the present invention, folding of a protein originally having disulfide bonds was properly carried out. Also, other proteins having disulfide bonds were examined so that substantially equivalent results were obtained.

Example 7

Synthesis of Murine Interleukin 6 (mIL 6)

Figure 5:
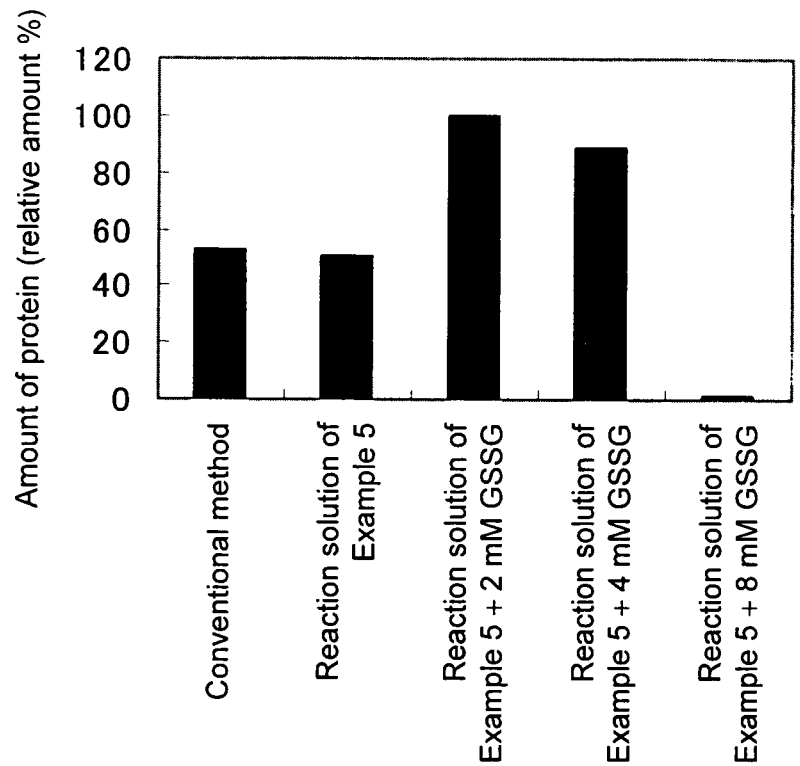
FIG. 5 shows the amounts of synthesized mIL6 protein.
Figure 6:
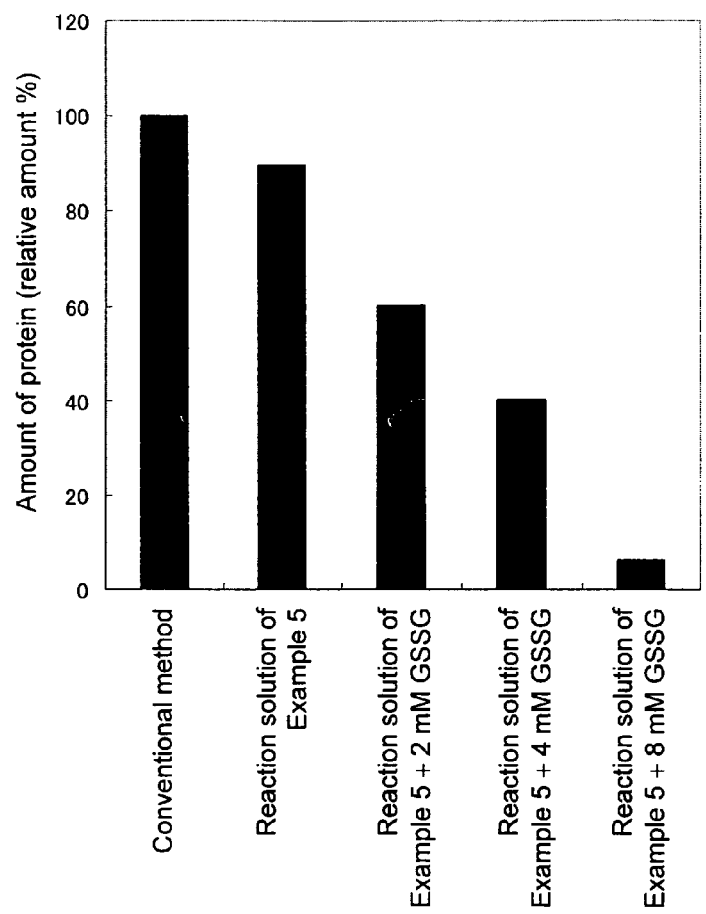
FIG. 6 shows the amounts of synthesized DHFR protein.

With the use of a mouse cDNA library, mIL6 was prepared in a manner similar to that used for Example 6. In addition, template DNA of *E. coli.* dihydrofolate reductase (DHFR) was prepared using *E. coli.* genomic DNA in a manner similar to that used for Example 6. Then, the following five types of reaction solutions were prepared: a reaction solution obtained by adding 1 mM of DTT to the protein synthesis reaction reagent of Example 5 (the conventional method); the protein synthesis reaction reagent of Example 5; and reaction solutions obtained by separately adding GSSG at final concentrations of 2, 4, and 8 mM to the reagent of Example 5. To each reaction solution, 1 pmol of template DNA was added, such that proteins corresponding to the respective reaction solutions were synthesized. In the case of DHFR synthesis, the reaction solutions were allowed to pass through ultrafilter membranes after protein synthesis. Then, the reaction solutions of DHFR synthesis and the reaction solutions of mIL6 synthesis were separately subjected to SDS-PAGE, followed by fluorescent staining of proteins with SYPRO Red. Staining patterns were analyzed using a fluoroimager so that amounts of proteins in the reaction solutions could be calculated based on color depth of mIL6 and that of DHFR. FIGS. 5 and 6 show the amounts of mIL6 proteins obtained and those of DHFR proteins obtained, respectively. As is apparent from FIGS. 5 and 6, when DHFRs having no intramolecular disulfide bonds were synthesized, the largest amounts of proteins were produced by the conventional method and the amounts of protein synthesized by the method of the present invention were less. On the other hand, it was confirmed that, when mIL6 having intramolecular disulfide bonds was synthesized, the amounts of proteins produced by the method of the present invention exceeded those produced by the conventional method. In addition, the same experiment was carried out except that template DNA of a different protein having disulfide bonds was used instead of template DNA of mIL6. Accordingly, substantially equivalent results were obtained.

Example 8

Influence of Protein Disulfide Isomerase (PDI)

Figure 7:
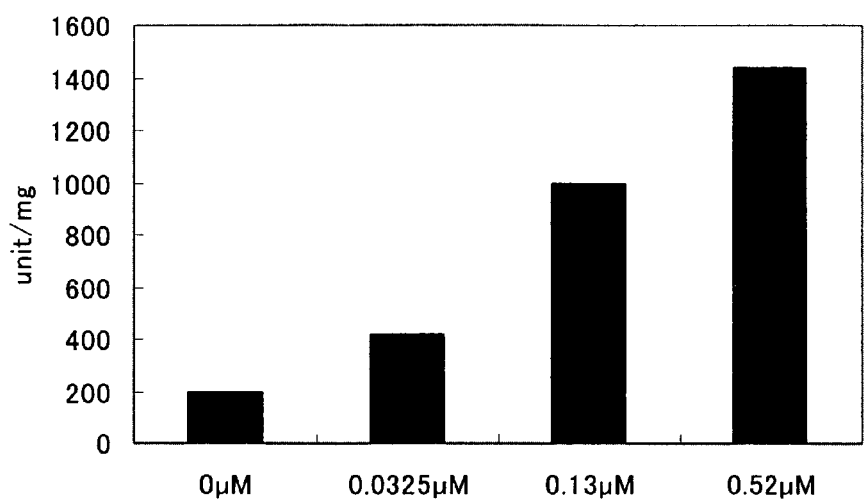
FIG. 7 shows specific activities of synthesized human lysozymes (influence of PDI concentration).

Four reaction solutions were prepared, each of which contained the protein synthesis reaction reagent of Example 5 with addition of 2 mM GSSG. Then, bovine-derived PDI (Takara Bio Inc.) was added to the reaction solutions to final concentrations of 0, 0.0325, 0.13, and 0.52 μM, respectively. Thereafter, template DNA of human lysozyme (1 pmol) was added to 50 μl of each reaction solution, resulting in protein synthesis. The specific activities of lysozymes were determined in a manner similar to that used for Example 6. FIG. 7 shows relationships between concentrations of PDI added to the reaction systems and specific activities of human lysozymes synthesized. As is apparent from FIG. 7, specific activities of proteins having disulfide bonds were found to be improved with addition of PDI to a concentration of 0.0325 μM or more. Further, it was confirmed that PDI activity can be determined by the method of the present invention. In addition, when other types of PDIs and disulfide interchange proteins were used instead of bovine PDI, substantially equivalent results were obtained.

Example 9

Influence of Dithiothreitol (DTT) Concentration

Figure 8:
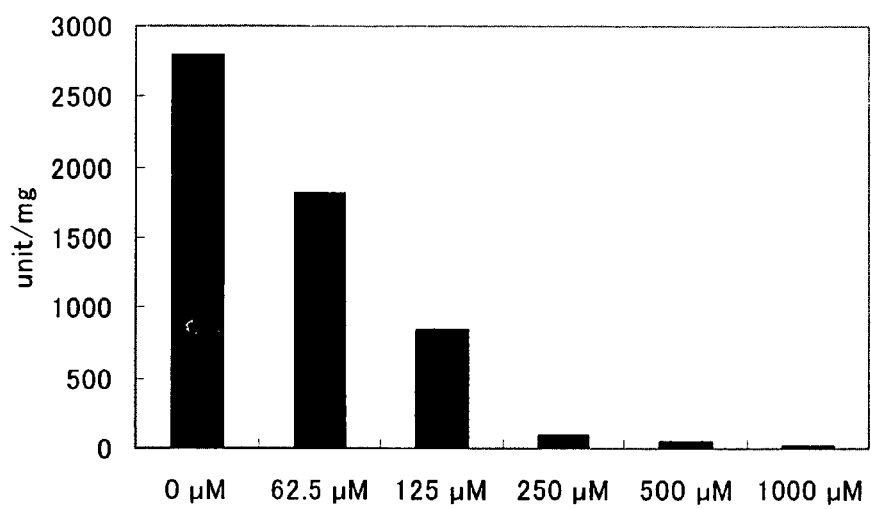
FIG. 8 shows specific activities of synthesized human lysozymes (influence of DTT concentration in the presence of 0.13 µM PDI).

Six reaction solutions were prepared, each of which contained the protein synthesis reaction reagent of Example 5 with addition of 0.13 μM PDI. Then, DTT was added to the reaction solutions to final concentrations of 1000, 500, 250, 125, 62.5, and 0 μM, respectively. Thereafter, 1 pmol of template DNA of human lysozyme was added to 50 μl of each reaction solution, resulting in protein synthesis. The specific activities of lysozymes were determined in a manner similar to that used for Example 6. FIG. 8 shows the results. As is apparent from FIG. 8, it was revealed that, with a DTT concentration of 125 μM or less, strong lysozyme activity can be obtained.

Example 10

Synthesis of Alkaline Phosphatase

Figure 9:
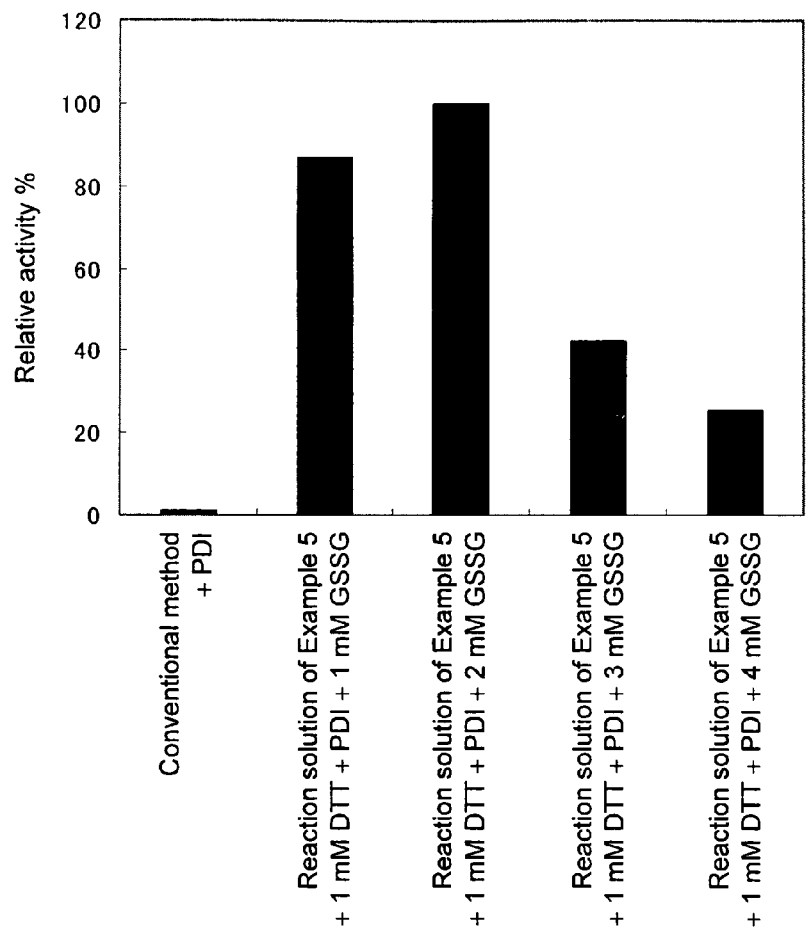
FIG. 9 shows activities of synthesized alkaline phosphatase (influence of GSSG concentration in the presence of 0.13 µM PDI and 1 mM DTT).
Figure 10:
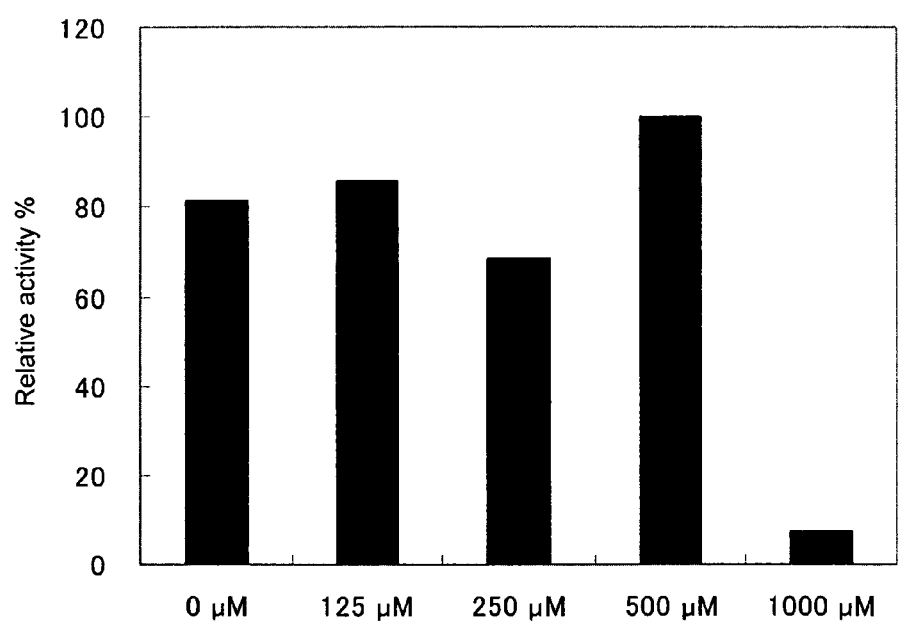
FIG. 10 shows activities of synthesized alkaline phosphatase (influence of DTT concentration difference in the presence of PDI).

Alkaline phosphatase is a protein having two intramolecular disulfide bonds, and thus it has long been deeply examined as a model protein with regard to the relationship between disulfide bond formation and the enzyme activity. Herein, alkaline phosphatase was synthesized.
PCR primers specific to E. coli genomic DNA and E. coli. alkaline phosphatase were used to produce template DNA of E. coli. alkaline phosphatase in a manner similar to that used for Example 6. Five reaction solutions were prepared, each of which contained the protein synthesis reaction reagent of Example 5 with the addition of 1 mM DTT and 0.13 μM PDI. Then, GSSG was added to the reaction solutions to concentrations of 0, 1, 2, 3, and 4 mM, respectively.
Thereafter, 1 pmol of template DNA of alkaline phosphatase gene was added to 50 μl of each reaction solution, resulting in protein synthesis. Concentrations of synthesized proteins were measured in a manner similar to that used for Example 5. Activities of synthesized alkaline phosphatases were determined by measuring the absorbance at 405 nm using p-nitrophenyl phosphate disodium salt as a substrate (Biochim Biophys Acta. 258:178-87 (1972). FIG. 9 shows relative activities of alkaline phosphatases. As is apparent from FIG. 9, no activity of alkaline phosphatase was obtained by the conventional method; that is to say, with the use of a protein reaction reagent with addition of 1 mM DTT and 0.13 μM PDI. On the other hand, the activity of alkaline phosphatase was obtained by the method of the present invention; that is to say, with the use of a reaction solution with addition of 1 mM or 2 mM GSSG. Even with the presence of 1 mM DTT in a system, the activity of alkaline phosphatase was confirmed. Thus, the occurrence of proper folding of synthesized proteins was revealed. In addition, different reaction solutions were prepared, containing the reaction solution of Example 5 and DTT at concentrations of 1000, 500, 250, 125, and 0 μM, respectively. As described above, template DNA was added to each reaction solution, followed by protein synthesis. Then, activities of alkaline phosphatase were determined. The results are shown in FIG. 10. In the absence of PDI, DTT concentrations were exclusively changed: Accordingly, it was revealed that the activity of alkaline phosphatase was obtained at a DTT concentration of 500 μM or less.

Example 11

Influence of DsbC

Figure 11:
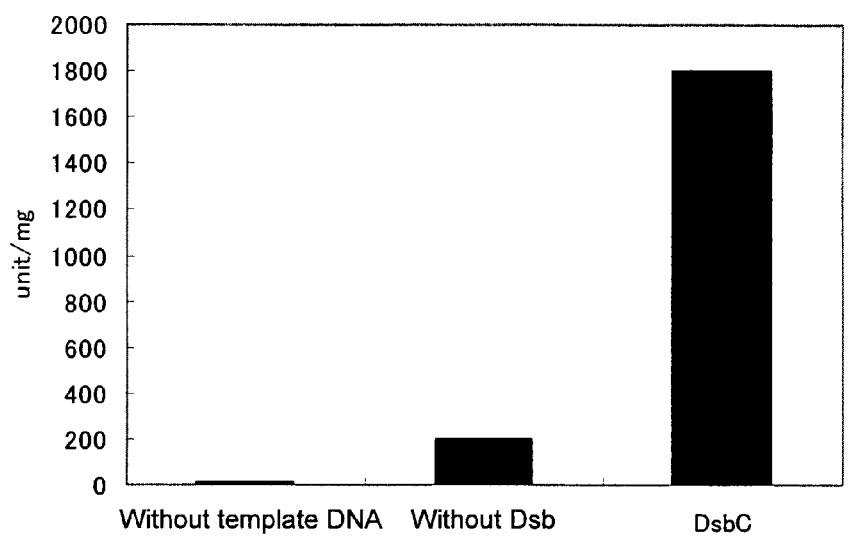
FIG. 11 shows activities of synthesized lysozyme (influence of addition or no addition of DsbC).

E. coli DsbC was amplified by PCR and a vector hyperexpressing dsbC was constructed in a manner similar to that used for Example 2, except that a DNA fragment having a sequence recognized by BamHI at the 5' end and HindIII at the 3' end was obtained. With the use of the obtained vector, E. coli. BL21/pREP4 was transformed. Then, purified DsbC was obtained in a manner similar to that used for Example 4. The protein purity was 90% or more. Three reaction solutions (50 μl each) were prepared by adding 1 mM DTT and 2 mM GSSG to the protein synthesis reagent of Example 5. To these reaction solutions, DsbC and template DNA of the human lysozyme gene of Example 6 were added at concentrations of 0, 0, and 0.5 μM and at concentrations of 0, 1, and 1 pmol, respectively. Amounts of synthesized proteins and activities of lysozyme were determined in a manner similar to that used for Example 6. FIG. 11 shows the specific activities. As is apparent from FIG. 11, it was revealed that addition of DsbC causes significant increase in the specific activity of lysozyme. In addition, when other disulfide interchange proteins were used instead of DsbC, and also when different types of disulfide interchange proteins were simultaneously used, substantially equivalent results were obtained.

Example 12

Figure 12:
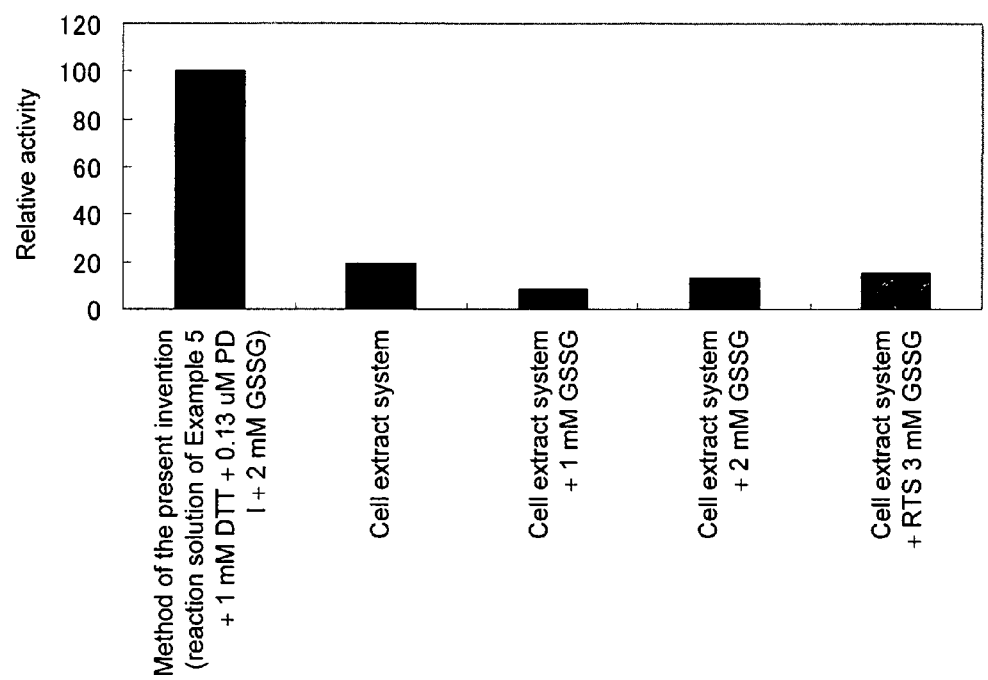
FIG. 12 shows activities of synthesized alkaline phosphatase (comparison between the method of the present invention and a method using a cell extract).

Comparison Between the Protein Synthesis Reagents of the Present Invention and Conventional Cell Extracts In accordance with the manufacturer's instructions, E. coli alkaline phosphatase was synthesized, except that GSSG was added to final concentrations of 0, 1, 2, and 3 mM using an in vitro protein synthesizing system (Roche Rapid Translation System 100) in which a cell extract of E. coli was used. In addition, E. coli alkaline phosphatase was synthesized by the method of the present invention in a manner similar to that used for Example 10. FIG. 12 shows specific activities of synthesized alkaline phosphatases. As is apparent from FIG. 12, in the system using a cell extract of E. coli, no activity of alkaline phosphatase was found, even with addition of GSSG at various concentrations, while on the other hand, the activity of alkaline phosphatase at a high level was confirmed by the synthesis method of the present invention.

Example 13

Confirmation of Purities of EF-Tu, DsbA, and DsbC

Figure 13:
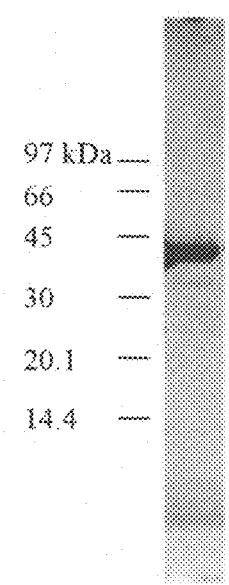
FIG. 13 shows an electrophoresis image of EF-Tu elution fraction.

Cells in which proteins comprising EF-Tu with His-Tag were expressed were sonicated in ice so as to be suspended in a loading buffer (300 mM NaCl, 50 mM NaH2PO4, pH 8.0). Then, the resulting cell lysate was subjected to centrifugation (30,000 g, 4° C., 30 minutes). Then, 50% Ni$^{2+}$-NTA slurry (Qiagen), which had been equilibrated in the ice-cooled loading buffer, was added to the supernatant obtained above, followed by stirring at 4° C. for 1 hour. Thereafter, resin was loaded into a column, followed by washing at 4° C. using the loading buffer (containing 10 mM imidazole, pH 8.0) in a volume 20 times that of the column. Using a loading buffer in a volume 20 times that of the column, proteins of interest were eluted from the column with an imidazole concentration gradient of 10 to 250 mM. Then, fractions (1 ml each) were collected. Proteins of interest were confirmed via SDS-PAGE. The electrophoresis pattern of each lane was read using a densitometer such that the purity was calculated. FIG. 13 shows electrophoresis images of EF-Tu elution fractions. The electrophoresis pattern of each lane was read using a densitometer, followed by collection of Ef-Tu fractions having purities of 90% or more.

Figure 14:
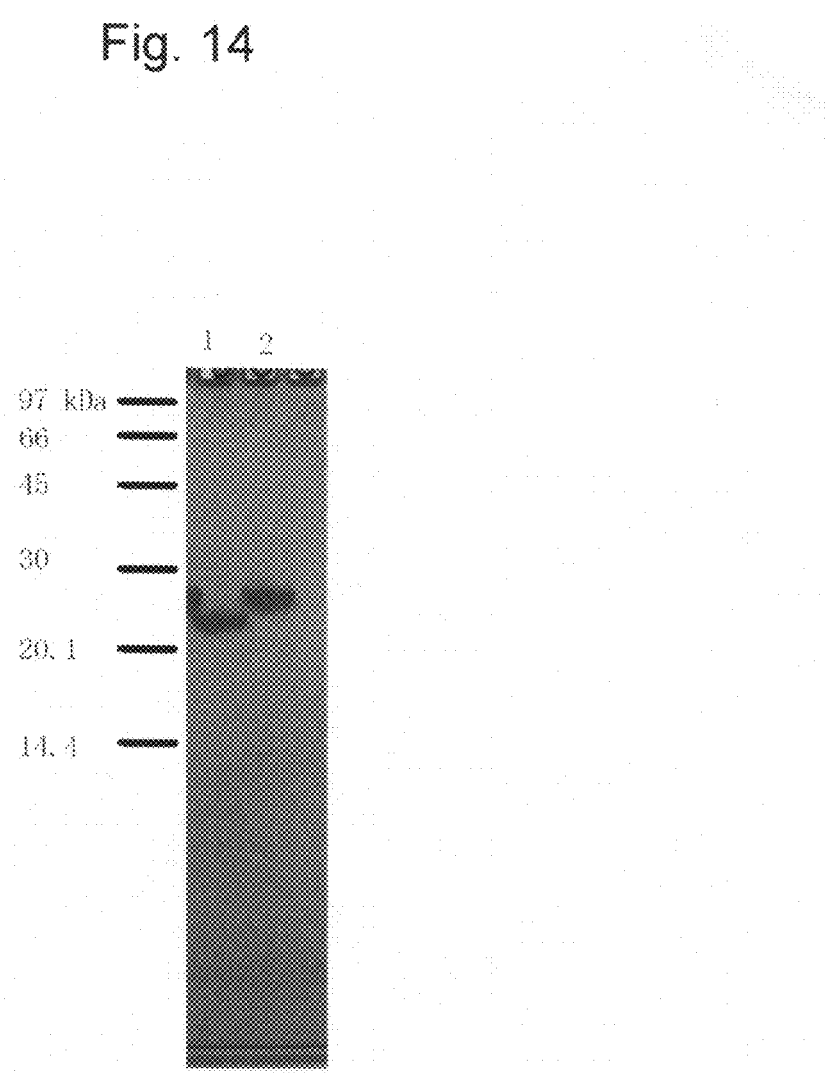
FIG. 14 shows an electrophoresis image of purified DsbA (lane 1) and DsbC (lane 2).

In addition, FIG. 14 shows electrophoresis images of purified DsbA (lane 1) and DsbC (lane 2). Both enzymes had purities of 90% or more.

INDUSTRIAL APPLICABILITY

Protein Synthesis Method

In accordance with the present invention, DTT that preferably has been removed from a conventional reaction solution may be added to a concentration of several micrometers to 1 mM. In addition, it is also possible not to add any DTT.

Further, in accordance with the conventional method using a cell-free protein synthesizing system from which DTT has been removed, it has been generally considered that amounts of synthesized proteins would decrease under the conditions of such system and synthesis efficiency of proteins of interest which have activity would deteriorate even if disulfide bonds could be formed in proteins. However, in accordance with the present invention, with the use of the reconstituted protein synthesizing system, amounts of synthesized proteins remain stable or increase in some cases. Thus, proteins can be synthesized with improved efficiency.

[Enzyme Assay]

In accordance with the method of activity measurement of the present invention, substrates are synthesized as single-strand polypeptides having no disulfide bond as a result of a protein synthesis reaction so that steps of reduction and denaturation are not required. Thus, upon synthesis or after synthesis, enzymes for activity measurement are added such that activities or structures of folded proteins are regarded as indicators. Therefore, the method of the present invention is characterized in that the steps and the time required can be significantly simplified and shortened compared with the conventional method.

All publications, patents, and patent applications cited herein are incorporated herein by reference in their entirety.

The invention claimed is:

1. A method of synthesizing a protein having intermolecular or intramolecular disulfide bonds, comprising using a reaction system comprising a), b), c), and d) below:
   a) at least one template nucleic acid encoding a protein of interest,
   b) a protein synthesis reaction reagent comprising 1) synthesized or isolated ribosomes, initiation factors, elongation factors, termination factors, aminoacyl-tRNA synthetases, methionyl tRNA transformylases, tRNAs, amino acids, ribonucleoside triphospates, 10-formyl 5,6,7,8-tetrahyrofolic acid (FD), salts and water or 2) synthesized or isolated ribosomes, initiation factors, elongation factors, aminoacyl-tRNA synthetases, methionyl tRNA transformylases, tRNAs, amino acids, ribonucleoside triphosphates, 10-formyl 5,6,7,8-tetrahydrofolic acid (FD), salts, and water,
   c) at least one purified oxidoreductase, and
   d) an effective amount of a purified dithiothreitol and at least one purified redox reagent,
   adding c) the at least one purified oxidoreductase for catalyzing oxidation-reduction of disulfide bonds d) the purified dithiothreitol and the at least one redox reagent for conditioning a redox state of disulfide bonds to b) the protein synthesis reaction reagent;
   thereafter adding the template nucleic acid a) to the protein synthesis reaction reagent b), thereby causing a reaction to synthesize a protein encoded by the template nucleic acid; and
   allowing the synthesized protein to form intermolecular or intramolecular disulfide bonds.

2. The method of synthesizing a protein according to claim 1, wherein the oxidoreductase is an enzyme catalyzing promotion and/or isomerization of disulfide bonds of the protein.

3. The method of synthesizing a protein according to claim 1, wherein the oxidoreductase consists of protein disulfide isomerases (PDIs) or disulfide interchange proteins.

4. The method of synthesizing a protein according to claim 3, wherein the concentration of protein disulfide isomerase is is 0.001 to 10 µM.

5. The method of synthesizing a protein according to claim 3, wherein the concentration of disulfide interchange protein is 0.01 to 10 µM.

6. The method of synthesizing a protein according to claim 1, wherein the reaction system comprises thioredoxin reductase at a concentration in the reaction system which is not more than 100 ng/ml.

7. The method of synthesizing a protein according to claim 1, wherein the reaction system comprises glutathione reductase at a concentration in the reaction system which is not more than 100 ng/ml.

8. The method of synthesizing a protein according to claim 1, wherein the redox reagent is oxidized glutathione.

9. The method of synthesizing a protein according to claim 8, wherein a ratio of a concentration of oxidized glutathione to dithiothreitol (oxidized glutathione:dithiothreitol) is 1:1 to 4:1.

10. The method of synthesizing a protein according to claim 1, wherein the purified oxidoreductase comprises DsbA and DsbC.

11. The method of synthesizing a protein according to claim 1, wherein the purified oxidoreductase consists of DsbA and DsbC.

* * * * *

```
                        SEQUENCE LISTING

<160> NUMBER OF SEQ ID NOS: 14

<210> SEQ ID NO 1
<211> LENGTH: 36
<212> TYPE: DNA
<213> ORGANISM: Artificial Sequence
<220> FEATURE:
<223> OTHER INFORMATION: Synthetic primer

<400> SEQUENCE: 1
aaggagatat accaatgaag gtctttgaaa ggtgtg                             36

<210> SEQ ID NO 2
<211> LENGTH: 37
<212> TYPE: DNA
<213> ORGANISM: Artificial Sequence
<220> FEATURE:
<223> OTHER INFORMATION: Synthetic primer

<400> SEQUENCE: 2
ggattagtta ttcattacac tccacaacct tgaacat                            37

<210> SEQ ID NO 3
<211> LENGTH: 85
<212> TYPE: DNA
<213> ORGANISM: Artificial Sequence
<220> FEATURE:
<223> OTHER INFORMATION: Synthetic primer

<400> SEQUENCE: 3
gaaattaata cgactcacta tagggagacc acaacggttt ccctctagaa ataattttgt    60
ttaactttaa gaaggagata tacca                                         85

<210> SEQ ID NO 4
```

<211> LENGTH: 495
<212> TYPE: DNA
<213> ORGANISM: Homo sapiens

<400> SEQUENCE: 4

```
gaaattaata cgactcacta tagggagacc acaacggttt ccctctagaa ataattttgt      60
ttaactttaa gaaggagata taccaatgaa ggtctttgaa aggtgtgagt tggccagaac     120
tctgaaaaga ttgggaatgg atggctacag gggaatcagc ctagcaaact ggatgtgttt     180
ggccaaatgg gagagtggtt acaacacacg agctacaaac tacaatgctg agacagaag      240 cactgattat gggatatttc agatcaatag ccgctactgg tgtaatgatg caaaacccc      300 aggagcagtt aatgcctgtc atttatcctg cagtgctttg ctgcaagata acatcgctga    360
tgctgtagct tgtgcaaaga gggttgtccg tgatccacaa ggcattagag catgggtggc    420
atggagaaat cgttgtcaaa acagagatgt ccgtcagtat gttcaaggtt gtggagtgta    480
atgaataact aatcc                                                      495
```

<210> SEQ ID NO 5
<211> LENGTH: 510
<212> TYPE: PRT
<213> ORGANISM: Bos taurus

<400> SEQUENCE: 5

```
Met Leu Arg Arg Ala Leu Leu Cys Leu Ala Leu Thr Ala Leu Phe Arg
1               5                   10                  15

Ala Gly Ala Gly Ala Pro Asp Glu Glu Asp His Val Leu Val Leu His
            20                  25                  30

Lys Gly Asn Phe Asp Glu Ala Leu Ala Ala His Lys Tyr Leu Leu Val
        35                  40                  45

Glu Phe Tyr Ala Pro Trp Cys Gly His Cys Lys Ala Leu Ala Pro Glu
    50                  55                  60

Tyr Ala Lys Ala Ala Gly Lys Leu Lys Ala Glu Gly Ser Glu Ile Arg
65                  70                  75                  80

Leu Ala Lys Val Asp Ala Thr Glu Glu Ser Asp Leu Ala Gln Gln Tyr
                85                  90                  95

Gly Val Arg Gly Tyr Pro Thr Ile Lys Phe Phe Lys Asn Gly Asp Thr
            100                 105                 110

Ala Ser Pro Lys Glu Tyr Thr Ala Gly Arg Glu Ala Asp Asp Ile Val
        115                 120                 125

Asn Trp Leu Lys Lys Arg Thr Gly Pro Ala Ala Ser Thr Leu Ser Asp
    130                 135                 140

Gly Ala Ala Ala Glu Ala Leu Val Glu Ser Ser Glu Val Ala Val Ile
145                 150                 155                 160

Gly Phe Phe Lys Asp Met Glu Ser Asp Ser Ala Lys Gln Phe Phe Leu
                165                 170                 175

Ala Ala Glu Val Ile Asp Asp Ile Pro Phe Gly Ile Thr Ser Asn Ser
            180                 185                 190

Asp Val Phe Ser Lys Tyr Gln Leu Asp Lys Asp Gly Val Val Leu Phe
        195                 200                 205

Lys Lys Phe Asp Glu Gly Arg Asn Asn Phe Glu Gly Glu Val Thr Lys
    210                 215                 220

Glu Lys Leu Leu Asp Phe Ile Lys His Asn Gln Leu Pro Leu Val Ile
225                 230                 235                 240

Glu Phe Thr Glu Gln Thr Ala Pro Lys Ile Phe Gly Gly Glu Ile Lys
                245                 250                 255
```

```
Thr His Ile Leu Leu Phe Leu Pro Lys Ser Val Ser Asp Tyr Glu Gly
            260                 265                 270

Lys Leu Ser Asn Phe Lys Lys Ala Glu Ser Phe Lys Gly Lys Ile
        275                 280                 285

Leu Phe Ile Phe Ile Asp Ser Asp His Thr Asp Asn Gln Arg Ile Leu
    290                 295                 300

Glu Phe Phe Gly Leu Lys Lys Glu Cys Pro Ala Val Arg Leu Ile
305                 310                 315                 320

Thr Leu Glu Glu Glu Met Thr Lys Tyr Lys Pro Glu Ser Asp Glu Leu
                325                 330                 335

Thr Ala Glu Lys Ile Thr Glu Phe Cys His Arg Phe Leu Glu Gly Lys
            340                 345                 350

Ile Lys Pro His Leu Met Ser Gln Glu Leu Pro Asp Asp Trp Asp Lys
        355                 360                 365

Gln Pro Val Lys Val Leu Val Gly Lys Asn Phe Glu Glu Val Ala Phe
    370                 375                 380

Asp Glu Lys Lys Asn Val Phe Val Glu Phe Tyr Ala Pro Trp Cys Gly
385                 390                 395                 400

His Cys Lys Gln Leu Ala Pro Ile Trp Asp Lys Leu Gly Glu Thr Tyr
                405                 410                 415

Lys Asp His Glu Asn Ile Val Ile Ala Lys Met Asp Ser Thr Ala Asn
            420                 425                 430

Glu Val Glu Ala Val Lys Val His Ser Phe Pro Thr Leu Lys Phe Phe
        435                 440                 445

Pro Ala Ser Ala Asp Arg Thr Val Ile Asp Tyr Asn Gly Glu Arg Thr
    450                 455                 460

Leu Asp Gly Phe Lys Lys Phe Leu Glu Ser Gly Gly Gln Asp Gly Ala
465                 470                 475                 480

Gly Asp Asp Asp Asp Leu Glu Asp Leu Glu Glu Ala Glu Glu Pro Asp
                485                 490                 495

Leu Glu Glu Asp Asp Asp Gln Lys Ala Val Lys Asp Glu Leu
            500                 505                 510

<210> SEQ ID NO 6
<211> LENGTH: 508
<212> TYPE: PRT
<213> ORGANISM: Homo sapiens

<400> SEQUENCE: 6

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125
```

Leu Lys Lys Arg Thr Gly Pro Ala Ala Thr Thr Leu Pro Asp Gly Ala
130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335

Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
            500                 505

<210> SEQ ID NO 7
<211> LENGTH: 645
<212> TYPE: PRT
<213> ORGANISM: Homo sapiens

<400> SEQUENCE: 7

```
Met Arg Pro Arg Lys Ala Phe Leu Leu Leu Leu Leu Gly Leu Val
1               5                   10                  15

Gln Leu Leu Ala Val Ala Gly Ala Glu Gly Pro Asp Glu Asp Ser Ser
            20                  25                  30

Asn Arg Glu Asn Ala Ile Glu Asp Glu Glu Glu Glu Glu Glu Asp
        35                  40                  45

Asp Asp Glu Glu Glu Asp Asp Leu Glu Val Lys Glu Glu Asn Gly Val
    50                  55                  60

Leu Val Leu Asn Asp Ala Asn Phe Asp Asn Phe Val Ala Asp Lys Asp
65                      70                  75                  80

Thr Val Leu Leu Glu Phe Tyr Ala Pro Trp Cys Gly His Cys Lys Gln
                85                  90                  95

Phe Ala Pro Glu Tyr Glu Lys Ile Ala Asn Ile Leu Lys Asp Lys Asp
            100                 105                 110

Pro Pro Ile Pro Val Ala Lys Ile Asp Ala Thr Ser Ala Ser Val Leu
            115                 120                 125

Ala Ser Arg Phe Asp Val Ser Gly Tyr Pro Thr Ile Lys Ile Leu Lys
    130                 135                 140

Lys Gly Gln Ala Val Asp Tyr Glu Gly Ser Arg Thr Gln Glu Glu Ile
145                 150                 155                 160

Val Ala Lys Val Arg Glu Val Ser Gln Pro Asp Trp Thr Pro Pro Pro
                165                 170                 175

Glu Val Thr Leu Val Leu Thr Lys Glu Asn Phe Asp Glu Val Val Asn
            180                 185                 190

Asp Ala Asp Ile Ile Leu Val Glu Phe Tyr Ala Pro Trp Cys Gly His
            195                 200                 205

Cys Lys Lys Leu Ala Pro Glu Tyr Glu Lys Ala Ala Lys Glu Leu Ser
210                 215                 220

Lys Arg Ser Pro Pro Ile Pro Leu Ala Lys Val Asp Ala Thr Ala Glu
225                 230                 235                 240

Thr Asp Leu Ala Lys Arg Phe Asp Val Ser Gly Tyr Pro Thr Leu Lys
            245                 250                 255

Ile Phe Arg Lys Gly Arg Pro Tyr Asp Tyr Asn Gly Pro Arg Glu Lys
            260                 265                 270

Tyr Gly Ile Val Asp Tyr Met Ile Glu Gln Ser Gly Pro Pro Ser Lys
            275                 280                 285

Glu Ile Leu Thr Leu Lys Gln Val Gln Glu Phe Leu Lys Asp Gly Asp
290                 295                 300

Asp Val Ile Ile Ile Gly Val Phe Lys Gly Ser Asp Pro Ala Tyr
305                 310                 315                 320

Gln Gln Tyr Gln Asp Ala Ala Asn Asn Leu Arg Glu Asp Tyr Lys Phe
            325                 330                 335

His His Thr Phe Ser Thr Glu Ile Ala Lys Phe Leu Lys Val Ser Gln
            340                 345                 350

Gly Gln Leu Val Val Met Gln Pro Glu Lys Phe Gln Ser Lys Tyr Glu
            355                 360                 365

Pro Arg Ser His Met Met Asp Val Gln Gly Ser Thr Gln Asp Ser Ala
            370                 375                 380

Ile Lys Asp Phe Val Leu Lys Tyr Ala Leu Pro Leu Val Gly His Arg
385                 390                 395                 400

Lys Val Ser Asn Asp Ala Lys Arg Tyr Thr Arg Arg Pro Leu Val Val
            405                 410                 415

Val Tyr Tyr Ser Val Asp Phe Ser Phe Asp Tyr Arg Ala Ala Thr Gln
            420                 425                 430
```

Phe Trp Arg Ser Lys Val Leu Glu Val Ala Lys Asp Phe Pro Glu Tyr
          435                 440                 445

Thr Phe Ala Ile Ala Asp Glu Glu Asp Tyr Ala Gly Glu Val Lys Asp
      450                 455                 460

Leu Gly Leu Ser Glu Ser Gly Glu Asp Val Asn Ala Ala Ile Leu Asp
465                 470                 475                 480

Glu Ser Gly Lys Lys Phe Ala Met Glu Pro Glu Glu Phe Asp Ser Asp
                  485                 490                 495

Thr Leu Arg Glu Phe Val Thr Ala Phe Lys Lys Gly Lys Leu Lys Pro
              500                 505                 510

Val Ile Lys Ser Gln Pro Val Pro Lys Asn Asn Lys Gly Pro Val Lys
          515                 520                 525

Val Val Val Gly Lys Thr Phe Asp Ser Ile Val Met Asp Pro Lys Lys
      530                 535                 540

Asp Val Leu Ile Glu Phe Tyr Ala Pro Trp Cys Gly His Cys Lys Gln
545                 550                 555                 560

Leu Glu Pro Val Tyr Asn Ser Leu Ala Lys Lys Tyr Lys Gly Gln Lys
                  565                 570                 575

Gly Leu Val Ile Ala Lys Met Asp Ala Thr Ala Asn Asp Val Pro Ser
              580                 585                 590

Asp Arg Tyr Lys Val Glu Gly Phe Pro Thr Ile Tyr Phe Ala Pro Ser
          595                 600                 605

Gly Asp Lys Lys Asn Pro Val Lys Phe Glu Gly Gly Asp Arg Asp Leu
      610                 615                 620

Glu His Leu Ser Lys Phe Ile Glu His Ala Thr Lys Leu Ser Arg
625                 630                 635                 640

Thr Lys Glu Glu Leu
                  645

<210> SEQ ID NO 8
<211> LENGTH: 517
<212> TYPE: PRT
<213> ORGANISM: Saccharomyces cerevisiae

<400> SEQUENCE: 8

Met Gln Val Thr Thr Arg Phe Ile Ser Ala Ile Val Ser Phe Cys Leu
1               5                   10                  15

Phe Ala Ser Phe Thr Leu Ala Glu Asn Ser Ala Arg Ala Thr Pro Gly
              20                  25                  30

Ser Asp Leu Leu Val Leu Thr Glu Lys Lys Phe Lys Ser Phe Ile Glu
          35                  40                  45

Ser His Pro Leu Val Leu Val Glu Phe Phe Ala Pro Trp Cys Leu His
      50                  55                  60

Ser Gln Ile Leu Arg Pro His Leu Glu Glu Ala Ala Ser Ile Leu Lys
65                  70                  75                  80

Glu His Asn Val Pro Val Val Gln Ile Asp Cys Glu Ala Asn Ser Met
                  85                  90                  95

Val Cys Leu Gln Gln Thr Ile Asn Thr Tyr Pro Thr Leu Lys Ile Phe
              100                 105                 110

Lys Asn Gly Arg Ile Phe Asp Gly Gln Val Tyr Arg Gly Val Lys Ile
          115                 120                 125

Thr Asp Glu Ile Thr Gln Tyr Met Ile Gln Leu Tyr Glu Ala Ser Val
      130                 135                 140

Ile Tyr Leu Asn Ser Glu Asp Glu Ile Gln Pro Tyr Leu Glu Asn Ala
145                 150                 155                 160

```
Thr Leu Pro Val Val Ile Asn Arg Gly Leu Thr Gly Leu Asn Glu Thr
            165                 170                 175

Tyr Gln Glu Val Ala Leu Asp Leu Ala Glu Asp Tyr Val Phe Leu Ser
            180                 185                 190

Leu Leu Asp Ser Glu Asp Lys Ser Leu Ser Ile His Leu Pro Asn Thr
195                 200                 205

Thr Glu Pro Ile Leu Phe Asp Gly Asn Val Asp Ser Leu Val Gly Asn
210                 215                 220

Ser Val Ala Leu Thr Gln Trp Leu Lys Val Val Ile Leu Pro Tyr Phe
225                 230                 235                 240

Thr Asp Ile Glu Pro Asp Leu Phe Pro Lys Tyr Ile Ser Ser Asn Leu
                245                 250                 255

Pro Leu Ala Tyr Phe Phe Tyr Thr Ser Glu Glu Glu Leu Glu Asp Tyr
            260                 265                 270

Thr Asp Leu Phe Thr Gln Leu Gly Lys Glu Asn Arg Gly Gln Ile Asn
            275                 280                 285

Phe Ile Ala Leu Asn Ser Thr Met Phe Pro His His Val Arg Phe Leu
290                 295                 300

Asn Met Arg Glu Gln Phe Pro Leu Phe Ala Ile His Asn Met Ile Asn
305                 310                 315                 320

Asn Leu Lys Tyr Gly Leu Pro Gln Leu Pro Glu Glu Glu Tyr Ala Lys
                325                 330                 335

Leu Glu Lys Pro Gln Pro Leu Asp Arg Asp Met Ile Val Gln Leu Val
            340                 345                 350

Lys Asp Tyr Arg Glu Gly Thr Ala Lys Pro Ile Val Lys Ser Glu Glu
            355                 360                 365

Ile Pro Lys Glu Gln Lys Ser Asn Val Tyr Lys Ile Val Gly Lys Thr
            370                 375                 380

His Asp Asp Ile Val His Asp Asp Lys Asp Val Leu Val Lys Tyr
385                 390                 395                 400

Tyr Ala Thr Trp Cys Ile His Ser Lys Arg Phe Ala Pro Ile Tyr Glu
                405                 410                 415

Glu Ile Ala Asn Val Leu Ala Ser Asp Glu Ser Val Arg Asp Lys Ile
                420                 425                 430

Leu Ile Ala Glu Val Asp Ser Gly Ala Asn Asp Ile Leu Ser Phe Pro
            435                 440                 445

Val Thr Gly Tyr Pro Thr Ile Ala Leu Tyr Pro Ala Gly Asn Asn Ser
450                 455                 460

Lys Pro Ile Ile Phe Asn Lys Ile Arg Asn Leu Glu Asp Val Phe Glu
465                 470                 475                 480

Phe Ile Lys Glu Ser Gly Thr His His Ile Asp Gly Gln Ala Ile Tyr
                485                 490                 495

Asp Lys Leu His Gln Ala Lys Asp Ser Glu Val Ser Thr Glu Asp Thr
            500                 505                 510

Val His Asp Glu Leu
        515

<210> SEQ ID NO 9
<211> LENGTH: 208
<212> TYPE: PRT
<213> ORGANISM: E. coli

<400> SEQUENCE: 9

Met Lys Lys Ile Trp Leu Ala Leu Ala Gly Leu Val Leu Ala Phe Ser
1               5                   10                  15
```

```
Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
            35                  40                  45

Cys Pro His Cys Tyr Gln Phe Glu Glu Val Leu His Ile Ser Asp Asn
 50                  55                  60

Val Lys Lys Leu Pro Glu Gly Val Lys Met Thr Lys Tyr His Val
 65                  70                  75                  80

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
            115                 120                 125

Asp Val Phe Ile Asn Ala Gly Ile Lys Gly Glu Glu Tyr Asp Ala Ala
            130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
            165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Lys Lys
            195                 200                 205

<210> SEQ ID NO 10
<211> LENGTH: 236
<212> TYPE: PRT
<213> ORGANISM: E. coli

<400> SEQUENCE: 10

Met Lys Lys Gly Phe Met Leu Phe Thr Leu Leu Ala Ala Phe Ser Gly
 1               5                  10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
            35                  40                  45

Thr Val Leu Thr Asn Ser Gly Val Leu Tyr Ile Thr Asp Asp Gly Lys
 50                  55                  60

His Ile Ile Gln Gly Pro Met Tyr Asp Val Ser Gly Thr Ala Pro Val
 65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
            115                 120                 125

Ala Asp Tyr Asn Ala Leu Gly Ile Thr Val Arg Tyr Leu Ala Phe Pro
            130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
            165                 170                 175

Ser Val Ala Pro Ala Ser Cys Asp Val Asp Ile Ala Asp His Tyr Ala
            180                 185                 190
```

```
Leu Gly Val Gln Leu Gly Val Ser Gly Thr Pro Ala Val Val Leu Ser
            195                 200                 205

Asn Gly Thr Leu Val Pro Gly Tyr Gln Pro Lys Glu Met Lys Glu
            210                 215                 220

Phe Leu Asp Glu His Gln Lys Met Thr Ser Gly Lys
225                 230                 235

<210> SEQ ID NO 11
<211> LENGTH: 217
<212> TYPE: PRT
<213> ORGANISM: Salmonella typhimurium

<400> SEQUENCE: 11

Met Thr Met Asn Tyr Ala Arg Asp Leu Phe Ser Leu Lys Gly Ile Leu
1               5                   10                  15

Phe Ser Phe Leu Leu Ala Gly Cys Val Cys Pro Val Val Ala Gln Glu
            20                  25                  30

Trp Glu Ser Ile Thr Pro Pro Val Asp Ala Pro Ala Val Val Glu
            35                  40                  45

Phe Phe Ser Phe Tyr Cys Pro Pro Cys Tyr Ala Phe Ser Gln Thr Met
50                  55                  60

Gly Val Asp Gln Ala Ile Arg His Val Leu Pro Gln Gly Ser Arg Met
65                  70                  75                  80

Val Lys Tyr His Val Ser Leu Leu Gly Pro Leu Gly His Glu Leu Thr
                85                  90                  95

Arg Ala Trp Ala Leu Ala Met Val Met Lys Glu Thr Val Ile Glu
            100                 105                 110

Lys Ala Phe Phe Thr Ala Gly Met Val Glu Lys Arg Leu His Ser Pro
            115                 120                 125

Asp Asp Val Arg Arg Val Phe Met Ser Ala Thr Gly Ile Ser Arg Gly
130                 135                 140

Glu Tyr Asp Arg Ser Ile Lys Ser Pro Ala Val Asn Asp Met Val Ala
145                 150                 155                 160

Leu Gln Glu Arg Leu Phe Lys Glu Tyr Gly Val Arg Gly Thr Pro Ser
                165                 170                 175

Val Tyr Val Arg Gly Arg Tyr His Ile Asn Asn Ala Ala Phe Gly Ala
            180                 185                 190

Phe Ser Val Glu Asn Phe Arg Ser Arg Tyr Ala Ala Val Val Arg Lys
            195                 200                 205

Leu Leu Ala Gly Asn Pro Asp Ala Asp
            210                 215

<210> SEQ ID NO 12
<211> LENGTH: 232
<212> TYPE: PRT
<213> ORGANISM: Neisseria meningitidis

<400> SEQUENCE: 12

Met Lys Ser Arg His Leu Ala Leu Gly Val Ala Ala Leu Phe Ala Leu
1               5                   10                  15

Ala Ala Cys Asp Ser Lys Val Gln Thr Ser Val Pro Ala Asp Ser Ala
            20                  25                  30

Pro Ala Ala Ser Ala Ala Ala Pro Ala Gly Leu Val Glu Gly Gln
            35                  40                  45

Asn Tyr Thr Val Leu Ala Asn Pro Ile Pro Gln Gln Gln Ala Gly Lys
    50                  55                  60
```

```
Val Glu Val Leu Glu Phe Phe Gly Tyr Phe Cys Pro His Cys Ala His
 65                  70                  75                  80

Leu Glu Pro Val Leu Ser Lys His Ala Lys Ser Phe Lys Asp Asp Met
                 85                  90                  95

Tyr Leu Arg Thr Glu His Val Val Trp Gln Lys Glu Met Leu Thr Leu
            100                 105                 110

Ala Arg Leu Ala Ala Ala Val Asp Met Ala Ala Asp Ser Lys Asp
        115                 120                 125

Val Ala Asn Ser His Ile Phe Asp Ala Met Val Asn Gln Lys Ile Lys
130                 135                 140

Leu Gln Asn Pro Glu Val Leu Lys Lys Trp Leu Gly Glu Gln Thr Ala
145                 150                 155                 160

Phe Asp Gly Lys Lys Val Leu Ala Ala Tyr Glu Ser Pro Glu Ser Gln
                165                 170                 175

Ala Arg Ala Asp Lys Met Gln Glu Leu Thr Glu Thr Phe Gln Ile Asp
            180                 185                 190

Gly Thr Pro Thr Val Ile Val Gly Lys Tyr Lys Val Glu Phe Ala
        195                 200                 205

Asp Trp Glu Ser Gly Met Asn Thr Ile Asp Leu Leu Ala Asp Lys Val
210                 215                 220

Arg Glu Glu Gln Lys Ala Ala Gln
225                 230

<210> SEQ ID NO 13
<211> LENGTH: 485
<212> TYPE: PRT
<213> ORGANISM: Caenorhabditis elegans

<400> SEQUENCE: 13

Met Ser Leu Ser Val Ser Phe Ile Phe Leu Leu Val Ala Ser Ile Gly
 1               5                  10                  15

Ala Val Val Ala Asp Ser Glu Asn Val Leu Val Leu Thr Glu Ser Asn
                20                  25                  30

Phe Glu Glu Thr Ile Asn Gly Asn Glu Phe Val Leu Val Lys Phe Tyr
            35                  40                  45

Ala Pro Trp Cys Val His Cys Lys Ser Leu Ala Pro Lys Tyr Asp Glu
 50                  55                  60

Ala Ala Asp Leu Leu Lys Glu Gly Ser Asp Ile Lys Leu Ala Lys
 65                  70                  75                  80

Val Asp Ala Thr Glu Asn Gln Ala Leu Ala Ser Lys Phe Glu Val Arg
                 85                  90                  95

Gly Tyr Pro Thr Ile Leu Tyr Phe Lys Ser Gly Lys Pro Thr Lys Tyr
            100                 105                 110

Thr Gly Gly Arg Ala Thr Ala Gln Ile Val Asp Trp Val Lys Lys Lys
        115                 120                 125

Ser Gly Pro Thr Val Thr Thr Val Glu Ser Val Glu Gln Leu Glu Glu
130                 135                 140

Leu Lys Gly Lys Thr Arg Val Val Val Leu Gly Tyr Phe Lys Asp Ala
145                 150                 155                 160

Lys Ser Asp Ala Ala Thr Ile Tyr Asn Glu Val Ala Asp Ser Val Asp
                165                 170                 175

Asp Ala Phe Phe Ala Val Ala Gly Ser Ala Glu Val Ala Ala Ala
            180                 185                 190

Ser Leu Asn Glu Asp Gly Val Ala Leu Ile Arg Thr Asp Gly Asp Asp
        195                 200                 205
```

```
Ser Glu Thr Ser Thr Ile Ala Glu Ala Glu Ile Thr Asn Thr Ile Ala
    210                 215                 220

Leu Lys Gln Trp Leu His Ala Tyr Lys Leu Ser Ala Val Thr Glu Phe
225                 230                 235                 240

Thr His Glu Ser Ala Gln Glu Ile Val Gly Gly Asp Leu Lys Lys Phe
                245                 250                 255

His Phe Leu Ile Ile Arg Lys Ser Asp Ser Ser Phe Asp Glu Thr Ile
                260                 265                 270

Ala Lys Phe Thr Glu Val Ala Lys Lys Phe Arg Ala Lys Ile Val Phe
            275                 280                 285

Val Leu Leu Asp Val Asp Val Glu Glu Asn Ala Arg Ile Leu Glu Phe
        290                 295                 300

Leu Gly Val Asp Ala Lys Asn Thr Pro Ala Asn Arg Ile Val Ser Leu
305                 310                 315                 320

Ala Asp Gln Val Glu Lys Phe Lys Pro Gln Glu Gly Glu Asp Phe Glu
                325                 330                 335

Ala Phe Thr Asn Ser Tyr Leu Glu Gly Lys Ser Ala Gln Asp Leu Lys
                340                 345                 350

Ala Gln Asp Leu Pro Glu Asp Trp Asn Ala Leu Pro Val Lys Val Leu
            355                 360                 365

Val Ala Ser Asn Phe Asn Glu Ile Ala Leu Asp Glu Thr Lys Thr Val
        370                 375                 380

Phe Val Lys Phe Tyr Ala Pro Trp Cys Gly His Cys Lys Gln Leu Val
385                 390                 395                 400

Pro Val Trp Asp Glu Leu Ala Glu Lys Tyr Gly Ser Asn Pro Asn Val
                405                 410                 415

Val Ile Ala Lys Leu Asp Ala Thr Leu Asn Glu Leu Ala Asp Val Lys
                420                 425                 430

Val Asn Ser Phe Pro Thr Leu Lys Leu Trp Pro Ala Gly Ser Ser Thr
            435                 440                 445

Pro Val Asp Tyr Asp Gly Asp Arg Asn Leu Glu Lys Phe Glu Glu Phe
        450                 455                 460

Val Asn Lys Tyr Ala Gly Ser Ala Ser Glu Ser Glu Thr Ala Ser Gln
465                 470                 475                 480

Asp His Glu Glu Leu
                485

<210> SEQ ID NO 14
<211> LENGTH: 507
<212> TYPE: PRT
<213> ORGANISM: Datisca glomerata

<400> SEQUENCE: 14

Met Ala Ser Met Val Ser Phe Cys Phe Leu Leu Leu Phe Leu Ala Phe
1               5                   10                  15

Phe Ala Ser Ser Phe Asn Glu Ile Tyr Ala Glu Ser Glu Ser Glu Lys
            20                  25                  30

Glu Phe Val Leu Thr Leu Asp Lys Ser Asn Phe Phe Asp Thr Val Ser
        35                  40                  45

Lys His Asn Phe Ile Val Val Glu Phe Tyr Ala Pro Trp Cys Gly His
    50                  55                  60

Cys Lys Lys Leu Ala Pro Glu Tyr Glu Lys Ala Ala Ser Ile Leu Ser
65                  70                  75                  80

Ser His Asp Pro Pro Val Ile Leu Ala Lys Val Asp Ala Asn Glu Glu
                85                  90                  95
```

```
Ala Asn Lys Glu Leu Ala Ser Glu Phe Glu Val Arg Gly Phe Pro Thr
            100                 105                 110

Ile Lys Ile Leu Arg Asn Gly Gly Lys Ile Val Gln Glu Tyr Lys Gly
            115                 120                 125

Pro Arg Asp Ala Asp Gly Ile Val Asp Tyr Leu Lys Lys Gln Ser Gly
            130                 135                 140

Pro Pro Ser Ala Glu Ile Lys Ser Ile Glu Asp Ala Thr Asn Leu Val
145                 150                 155                 160

Ser Glu Lys Lys Ile Val Val Gly Ile Phe Pro Lys Phe Ser Gly
                165                 170                 175

Glu Glu Phe Glu Asn Phe Ser Ala Leu Ala Lys Leu Arg Ser Asp
            180                 185                 190

Tyr Glu Phe Gly His Thr Leu Asp Ala Lys Leu Leu Pro Arg Gly Glu
            195                 200                 205

Ser Ser Val Ser Gly Pro Val Arg Leu Phe Lys Pro Phe Asp Glu
            210                 215                 220

Leu Phe Val Asp Phe Gln Asp Phe Asp Val Asn Ala Leu Glu Lys Leu
225                 230                 235                 240

Val Glu Glu Ser Ser Val Pro Thr Val Thr Ile Phe Asp Lys Asp Pro
                245                 250                 255

Ser Asn His Pro Phe Val Val Lys Phe Phe Asn Asn Ala Asn Ala Lys
                260                 265                 270

Ala Met Leu Phe Leu Asn Phe Thr Ser Glu Val Val Glu Ser Phe Arg
            275                 280                 285

Ser Ile Tyr Arg Glu Val Ala Glu Lys Asn Lys Gly Glu Gly Ile Ser
            290                 295                 300

Phe Leu Ile Gly Asp Thr Glu Ser Ser Gln Gly Ala Phe Gln Tyr Phe
305                 310                 315                 320

Gly Leu Arg Asp Asp Gln Val Pro Leu Ile Val Ile Gln Asn Asn Asp
            325                 330                 335

Gly Thr Lys Tyr Leu Lys Pro Asn Leu Glu Pro Asp His Ile Ala Ser
            340                 345                 350

Trp Val Lys Glu Tyr Lys Asp Cys Lys Leu Ser Pro Tyr Arg Lys Ser
            355                 360                 365

Glu Pro Ile Pro Glu His Asn Asn Glu Pro Val Lys Val Val Ala
            370                 375                 380

Asp Ser Leu Asp Glu Ile Val Phe Lys Ser Gly Lys Asn Val Leu Leu
385                 390                 395                 400

Glu Phe Tyr Ala Pro Trp Cys Gly His Cys Lys Gln Leu Ala Pro Ile
            405                 410                 415

Leu Asp Glu Val Ala Val Ser Phe Glu Asn Asp Pro Val Leu Ile
            420                 425                 430

Ala Lys Leu Asp Ala Thr Ala Asn Asp Tyr Pro Thr Asn Thr Phe Asp
            435                 440                 445

Val Lys Gly Tyr Pro Thr Leu Tyr Phe Lys Ser Ala Ser Gly Glu Leu
            450                 455                 460

Leu Gln Tyr Asp Gly Gly Arg Thr Lys Glu Asp Phe Ile Glu Phe Ile
465                 470                 475                 480

Glu Lys Asn Arg Glu Lys Ser Ser Lys Glu Ser Ile Val Lys Asp
                485                 490                 495

Asp Gln Thr Asp Ser Gly Thr Lys Ala Glu Leu
                500                 505
```